US009664326B2

(12) United States Patent
Berube et al.

(10) Patent No.: US 9,664,326 B2
(45) Date of Patent: May 30, 2017

(54) APPARATUS AND METHOD FOR SEALING A PIPE INCLUDING INTERNAL AND EXTERNAL GRIPPING MEANS

(75) Inventors: Guy Berube, Sarnia (CA); Glenn Carson, Point Edward (CA)

(73) Assignee: CAR-BER Investments Inc., Wallaceburg (CA)

( * ) Notice: Subject to any disclaimer, the term of this patent is extended or adjusted under 35 U.S.C. 154(b) by 473 days.

(21) Appl. No.: 14/346,020

(22) PCT Filed: Sep. 6, 2012

(86) PCT No.: PCT/CA2012/050615
§ 371 (c)(1),
(2), (4) Date: Sep. 15, 2014

(87) PCT Pub. No.: WO2013/040699
PCT Pub. Date: Mar. 28, 2013

(65) Prior Publication Data
US 2014/0326324 A1    Nov. 6, 2014

Related U.S. Application Data

(60) Provisional application No. 61/536,625, filed on Sep. 20, 2011.

(51) Int. Cl.
*F16L 55/10* (2006.01)
*F16L 55/115* (2006.01)
(Continued)

(52) U.S. Cl.
CPC ......... *F16L 55/115* (2013.01); *F16L 55/1286* (2013.01); *F16L 55/136* (2013.01);
(Continued)

(58) Field of Classification Search
USPC .................................. 138/89, 90, 96 R, 96 T
See application file for complete search history.

(56) References Cited

U.S. PATENT DOCUMENTS 1,354,925 A * 10/1920 Svenson ............. G01M 3/2853
125/13.01
2,725,898 A * 12/1955 Stansbury .............. B65D 59/02
138/96 R
(Continued)

FOREIGN PATENT DOCUMENTS

EP    0103777 A1    3/1984

OTHER PUBLICATIONS

International Search Report pertaining to International Application No. PCT/CA2012/050615.

*Primary Examiner* — James Hook
(74) *Attorney, Agent, or Firm* — Marsh Fischmann & Breyfogle LLP; Jonathon A. Szumny

(57) ABSTRACT

A tool is provided for closing and sealing the open end of a pipe in connection with hydraulic pressure testing. The tool is inserted into the pipe lumen and can be operated from outside. It comprises inner and outer, opposed circumferential clamps; a front plate braced against the pipe end face; a movable back plate internal of the pipe lumen; and an O-ring, carried by the back plate, which can be squeezed by pressing the back plate against the inner clamp. Ports extend through the back plate to the upper and lower ends of its peripheral surface, for bottom filling and top venting of the pipe lumen.

2 Claims, 16 Drawing Sheets

(51) Int. Cl.
*F16L 55/128* (2006.01)
*F16L 55/136* (2006.01)
*G01M 3/02* (2006.01)
*G01M 3/28* (2006.01)
*G01N 3/12* (2006.01)

(52) U.S. Cl.
CPC .......... *G01M 3/022* (2013.01); *G01M 3/2815* (2013.01); *G01N 3/12* (2013.01); *Y10T 137/0379* (2015.04)

(56) References Cited

U.S. PATENT DOCUMENTS

| | | | | |
|---|---|---|---|---|
| 2,886,067 | A * | 5/1959 | Maxwell | F16L 55/115 138/90 |
| 3,179,127 | A * | 4/1965 | Terry | G01M 3/022 138/90 |
| 3,326,243 | A * | 6/1967 | Augustus | F16L 55/1286 138/90 |
| 3,647,108 | A * | 3/1972 | Kemp | F16J 13/12 138/90 |
| 3,765,560 | A * | 10/1973 | Kemp | F16J 13/06 138/90 |
| 3,998,245 | A * | 12/1976 | Martin | E03B 5/06 138/89 |
| 4,024,893 | A | 5/1977 | Jackman et al. | |
| 4,129,151 | A * | 12/1978 | Henson | E21B 33/03 138/89 |
| 4,377,185 | A * | 3/1983 | Katz | G01M 3/022 138/90 |
| 4,415,005 | A * | 11/1983 | Janzen | E21B 17/006 138/89 |
| 4,880,028 | A * | 11/1989 | Osburn | B25B 27/14 116/277 |
| 5,209,266 | A | 5/1993 | Hiemsoth | |
| 5,850,854 | A | 12/1998 | Carroll | |
| 7,669,899 | B2 * | 3/2010 | Carson | F16L 55/11 138/89 |
| 2011/0048112 | A1 | 3/2011 | Carson | |

* cited by examiner

APPARATUS AND METHOD FOR SEALING A PIPE INCLUDING INTERNAL AND EXTERNAL GRIPPING MEANS

CROSS REFERENCE TO RELATED APPLICATIONS

The present application claims priority under the Paris Convention to U.S. Application No. 61/536,625, filed Sep. 20, 2011, the entire contents of which are incorporated herein by reference.

FIELD OF THE INVENTION

The present invention relates to an apparatus and method for sealing an open end of a pipe. More particularly, the invention relates to an apparatus and method for sealing an end of a pipe with gripping means provided interiorly and exteriorly on the pipe wall. Once sealed, the apparatus and method allows the pipe to be pressurized for testing purposes etc.

BACKGROUND OF THE INVENTION

In chemical or petrochemical plants etc., it is common for fluid materials (e.g. liquids, gases etc.) to be conveyed from one location to another using equipment such as conduits or pipes (collectively referred to herein as "pipes"). Such pipes are often manufactured from metal sections that are joined together by welds. For example, when joining adjacent ends of pipe together, it is common for each end to be provided with a flange that is welded to the respective pipe end. Once each flange is thus secured to the pipes, they are then bolted together to form a sealed joint. Typically, a gasket or other such sealing means is provided between the opposed faces of the flanges. Such flanges may also be provided on nozzles secured, by welding, to holding tanks and other such vessels so that pipes can be connected thereto. Alternatively, the connections between lengths of pipe or other equipment may be welded directly together (i.e. butt welded) to form the seal. In either case, it will be appreciated that each welded joint or section must have integrity and form a complete seal so as to prevent leakage of the materials being transported. This is particularly important when handling potentially hazardous materials such as flammable or toxic liquids where leakage of such fluids can lead to catastrophic consequences. Therefore, for reasons of safety, it is often necessary to periodically test the integrity of the welds used in joining the various pieces of equipment (such as pipes, vessels, flanges and the like) together.

The prior art provides various tools for conducting weld integrity tests on conduits. Many of such known tools are used in pressure tests wherein a highly pressurized zone is created at least at the region of a weld being tested and such pressure monitored. In such tests, a drop in pressure signifies a failed weld. For example, U.S. Pat. Nos. 6,131,441 and 5,844,127 (the entire disclosures of which are incorporated herein by reference) teach weld testing tools that isolate a particular section of a pipe (such section including a weld) and subject the section to a high pressure fluid within a constrained annular space defined by the tool and the inner surface of the pipe. The pressure of the fluid within the annular space is monitored whereby a drop in such pressure signifies a leak in the weld.

U.S. Pat. Nos. 6,463,791 and 7,874,217 (the entire disclosures of which are incorporated herein by reference) also teach apparatuses for testing welds.

In some cases, it is necessary to seal an end of a pipe to conduct the above mentioned pressure test. In this regard, PCT Application number PCT/CA2011/050121 (the entire disclosure of which is incorporated herein by reference) provides a tool for sealing an end of a pipe that incorporates a gripper or clamp for engaging the exterior surface of the pipe. Similarly, PCT Application number PCT/CA2011/050122 (the entire disclosure of which is incorporated herein by reference) also provides a sealing tool for sealing an end of a pipe, which comprises a device that includes a gripping device for engaging both the interior and exterior portions of the pipe. The end sealing devices taught in these references may be used to seal one or both ends of a given pipe (or another opening such as the case with a pipe having a "T" junction). Once the device of PCT/CA2011/050121 or PCT/CA2011/050122 is secured to the one or more ends of the pipe, the interior of the pipe is then pressurized and the pressure monitored as indicated above. While the device taught in PCT/CA2011/050122 provides an efficient and effective sealing device for the ends of pipes, it may be difficult to handle when scaled for large diameter pipes (i.e. pipes greater than 24 inches or 36 inches in diameter) in view of its increased weight.

There exists a need for a device for sealing an end of a pipe, particularly large diameter pipes, and for conducting the type of weld integrity stress tests mentioned above. In particular, there is a need for an apparatus that can be easily mounted on an open end of a pipe so as to effectively seal the pipe opening and maintain such seal during pressurization of the pipe interior. Such pressurization may be associated with pipe integrity testing methods. Preferably, such apparatus would not subject the pipe to any significant damage.

SUMMARY OF THE INVENTION

In one aspect, the present invention generally provides an apparatus for sealing an open end of a pipe and for frictionally engaging or "gripping" the inner and outer surfaces of the pipe to prevent relative axial movement between the apparatus and the pipe.

In another aspect, the invention generally provides a method for sealing an open end of a pipe with a sealing apparatus and wherein the sealing apparatus frictionally engages or "grips" the inner and outer surfaces of the pipe to prevent relative axial movement between the sealing apparatus and the pipe.

In another aspect, the apparatus of the invention seals the open end of the pipe and pressurizes the pipe for conducting an integrity test thereof.

Thus, in one aspect, the invention provides an apparatus for sealing an open end of a pipe comprising:
  a front plate for positioning against the open end of the pipe;
  a back plate adapted for insertion within the pipe, the back plate including a first face, a second face and a perimeter, wherein, when in use, the first face faces the open end of the pipe and the second face faces the lumen of the pipe;
  a sealing member for forming a circumferential seal between the back plate and the inner surface of the pipe;
  a first gripping means for frictionally engaging the inner surface of the pipe;
  a second gripping means for frictionally engaging the outer surface of the pipe; and, one or more connecting means for connecting together the front plate, the back plate and the first and second gripping means and for urging the back plate towards the front plate;

wherein the first and second engagement means prevent relative axial movement between the apparatus and the pipe when the apparatus is in use;

and wherein the back plate includes two or more ports for providing a fluid connection into the pipe through the back plate, each of the ports having a first opening on the first face of the back plate and a second opening on the perimeter of the back plate, wherein, when the apparatus is in use, at least one of the ports is adapted to fill the pipe with a pressurizing fluid and another of the ports is adapted to vent the pipe.

In another aspect, the invention provides a method of sealing and pressurizing a generally horizontally oriented pipe having an open end, the method comprising:

closing and sealing the pipe with a sealing apparatus positioned adjacent the open end of the pipe;

anchoring the sealing apparatus to the pipe with a first gripping means, for frictionally engaging the inner surface of the pipe, and with a second gripping means, for frictionally engaging the outer surface of the pipe;

forming a circumferential seal between the inner surface of the pipe and the sealing apparatus;

filling the pipe with a pressurizing fluid through a first port provided on the sealing apparatus and venting the pipe during the pressurizing process with a second port provided on the sealing apparatus, the first port being positioned vertically below the second port.

BRIEF DESCRIPTION OF THE DRAWINGS

These and other features of the invention will become more apparent in the following detailed description in which reference is made to the appended drawings wherein.

DETAILED DESCRIPTION OF THE INVENTION

Throughout the description of the invention the following terms will be assumed to have the following associated meanings:

"Annular"—this term is used to describe a body having at least one outer diameter and at least one inner diameter. Thus, an "annular disc" will be assumed to be an object having an outer diameter and a central aperture thereby providing an inner diameter.

"Axial"—this term will be used to describe a direction taken along the longitudinal axis of a pipe or conduit. Thus, "axial force" or "axial stress" will be understood as being a force applied in a direction parallel to the longitudinal axis of the conduit. Similarly, the term "axially extending" will be understood to mean extending in a direction parallel to the longitudinal axis of the pipe.

"Radial"—this term will be used to describe a direction taken along the radius of the pipe or other object to which reference is made.

"Proximal" and "distal"—these terms will be used to describe the positions of various components of the invention once positioned over a pipe having an open end. The term "proximal" will be used to describe a position closer to the open end of the pipe. The term "distal" will be used to describe a position away from the open end of the pipe.

In general, the invention provides an apparatus that seals an end of a pipe. It will be understood that the pipe will have a generally circular cross section. The apparatus comprises at least one sealing member that engages the inner surface of the pipe wall and forms a seal between the pipe wall and the apparatus so as to prevent passage of fluids (i.e. liquids, gases, vapors etc.) from one side of the apparatus to the other. The apparatus also includes two gripping means to frictionally engage the inner and outer surfaces of the pipe wall, so as to prevent relative axial movement between the apparatus and the pipe. According to a method of the present invention, a pipe to be sealed is provided with an apparatus, such as that discussed above, which simultaneously grips the inner and outer surfaces of the pipe wall to prevent relative axial movement between the apparatus and the pipe. A seal is formed between the apparatus and the inner surface of the pipe to prevent passage of fluids from one side of the apparatus to the other. In a preferred embodiment, the apparatus of the invention is adapted for use with large diameter pipes (i.e. pipes having a diameter greater than 20 inches, including diameters of 36 inches or more). In particular, the apparatus of the preferred embodiment of the invention is designed to seal at least one end of a large diameter pipe and being designed to minimize weight so as to allow easy manipulation thereof.

Figure 1:
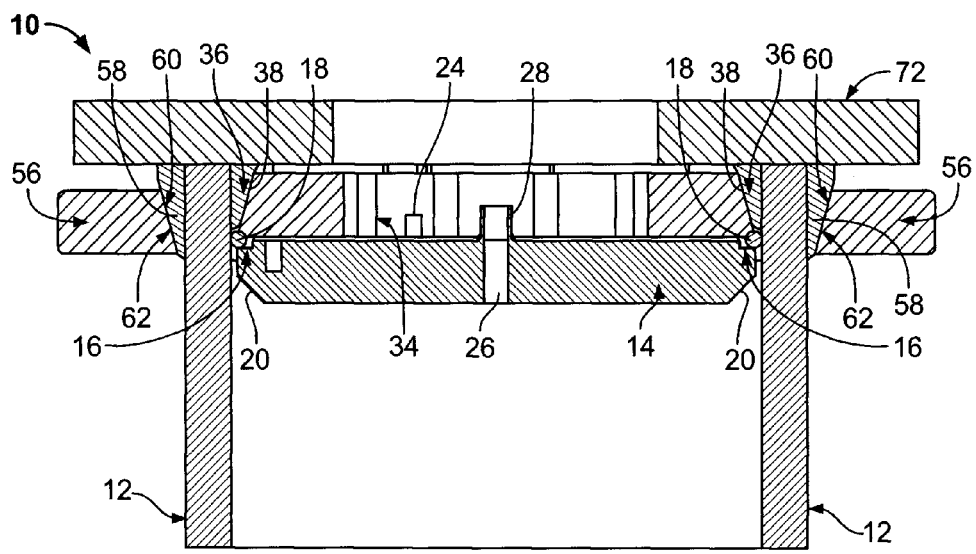
FIG. 1 is a schematic cross sectional view of an apparatus according to an aspect of the invention, in use within a pipe.

FIG. 1 illustrates an apparatus 10 according to one aspect of the invention, provided on an end of a pipe 12. As shown, the apparatus 10 comprises a back plate 14 that is adapted to be provided within the pipe 12, proximal to the end of the pipe 12 to be sealed. An embodiment of the back plate is further illustrated in FIGS. 2 to 6. In the illustrated embodiment, the back plate 14 comprises a generally solid body, preferably in the shape of a disc, having a first, or proximal end face 13 and a second, or distal end face 15. As will be understood, although the back plate 14 is illustrated in FIGS. 2 to 6 in the form of a disc shaped body, various other shapes of the back plate 14 would be possible, and some of such other embodiments are discussed further below. As shown in FIG. 1, the back plate 14 comprises, according to a preferred embodiment, a generally circular disc having an outer diameter that is sized to be positioned within the pipe 12 and axially aligned therewith. It will be understood that the back plate 14 and other components of the invention, particularly those adapted for insertion within a pipe, will be designed to allow for some clearance so as to accommodate any imperfections in the pipe wall. In addition, as discussed further below, a given dimension of the apparatus of the invention may be used for a range of similar diameter pipes.

The back plate 14 includes a groove or recess 16 at the first or proximal end face 13 (i.e. the end facing, or proximal to the opening of the pipe when the apparatus is in use) for receiving a sealing member 18, such as an O-ring and the like. As discussed further below, the sealing member 18 serves to form a fluid tight seal between the apparatus and the inner surface of the pipe when the apparatus is in use.

In a preferred embodiment, the second or distal end face 15 of the back plate 14 (i.e. the end facing away from, or distal to the opening of the pipe when the apparatus is in use) is provided with a radially inwardly directed bevel 20, whereby the radius of the back plate 14 is reduced in an axial direction towards the second end face 15 thereof. As will be understood, the bevel 20 serves to facilitate installation of the back plate 14 within the pipe 12 being tested, particularly since the outer diameter of the back plate 14 would preferably be close to the inner diameter of the pipe 12 being sealed. It will also be understood that the back plate 14 would equally function without the bevel 20.

Figure 2:
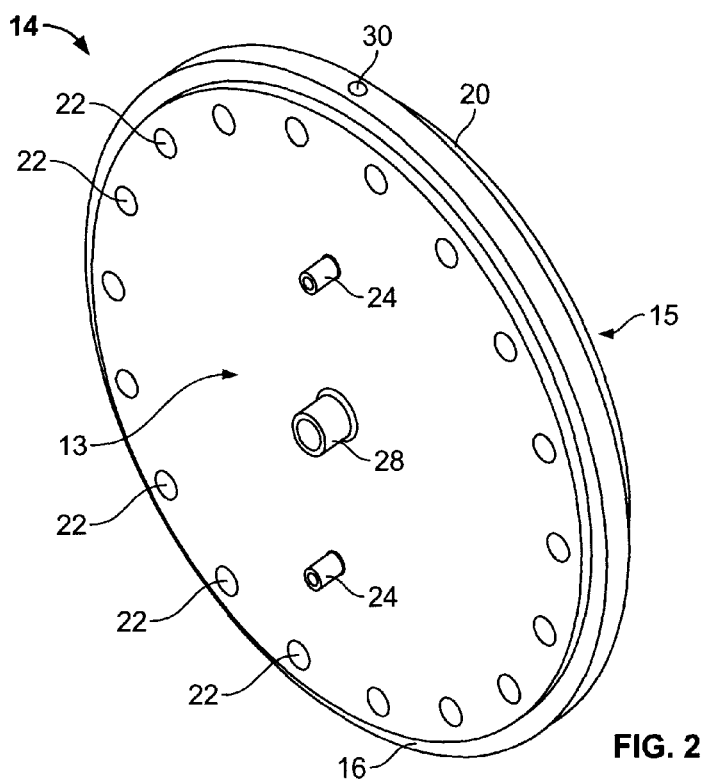
FIG. 2 is a front perspective view of a back plate according to an aspect of the invention.
Figure 3:
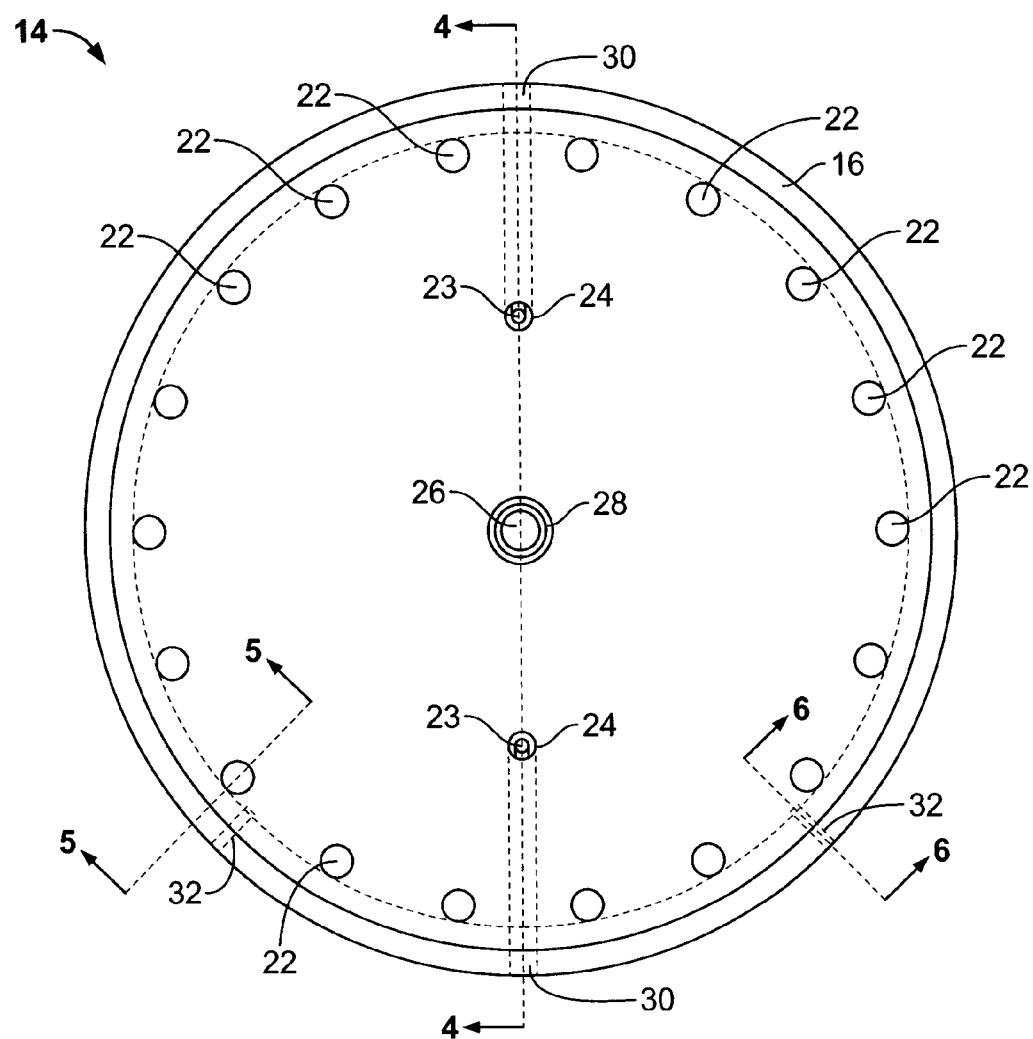
FIG. 3 is a front view of the back plate of FIG. 2.
Figure 4:
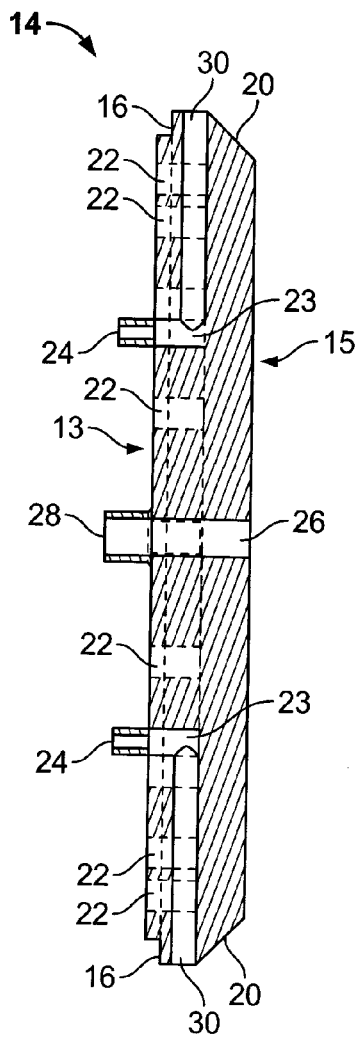
FIG. 4 is a side cross sectional view of the back plate shown in FIG. 3, taken along the line A-A thereof.
Figure 5:
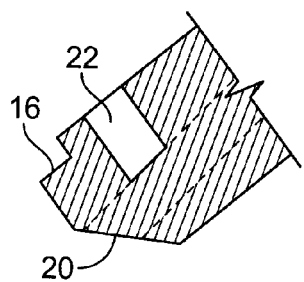
FIG. 5 is a partial cross sectional view of the back plate shown in FIG. 3, taken along the line B-B thereof.
Figure 6:
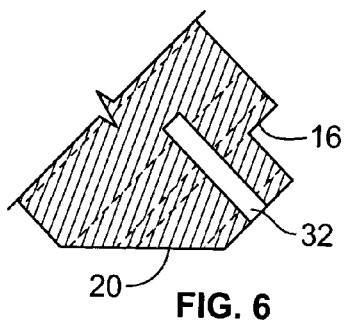
FIG. 6 is a magnified partial cross sectional view of the back plate shown in FIG. 3, taken along the line C-C thereof.

As more clearly shown in FIGS. 2 to 4, the back plate 14 is provided with a plurality of circumferentially spaced bolt holes 22. As illustrated in FIG. 4, the bolt holes 22 do not extend through the back plate 14. The bolt holes 22 are preferably tapped so as to provide a threaded inner surface therein, into which first bolts are screwed. Such first bolts are illustrated at 90 in FIG. 31 and discussed further below. In another embodiment, it will be understood that the first bolts may be permanently secured into the bolt holes 22 such as by welding and the like. As illustrated, the bolt holes 22 are preferably equidistantly spaced about the circumference of the back plate 14 at a specified radius thereof. The positioning of the bolt holes 22 corresponds to the positioning of bolt holes of other components of the apparatus, as discussed further below.

The first face 13 of the back plate 14 is also preferably provided with two or more first holes or ports 23. As shown in FIG. 4, the holes 23 do not extend through the width of the back plate 14. Therefore, the holes 23 do not protrude through the second face 15 thereof. In a preferred embodiment, two such holes 23 are provided on the back plate 14. The back plate 14 is further provided with two or more radially extending second, or radial holes 30, each of which extend radially through the outer perimeter of the back plate 14 and join with one of the first holes 23 described above so as to allow fluid communication between the first holes 23 and the second holes 30. In the result, the combination of the first holes 23 and second, radial holes 30 result in ports or fluid passages on the back plate 14. Such ports (23, 30) are used to provide fluid communication from the first face of the back plate 14 to the outer perimeter thereof, the purpose of which is described below. The first holes 23 may preferably be provided with couplings 24 that extend axially away from the first face 13 of back plate 14. When the apparatus is in use, the couplings 24 preferably extend towards the opening of the pipe for ease of use.

The second holes 30 are preferably provided on opposite ends of the perimeter of the back plate 14. That is, the second holes 30 are preferably provided approximately on opposite ends of a given diameter of the back plate 14. With such arrangement, and when the apparatus is in use, the back plate 14 may be oriented so that the second holes 30 are positioned in opposite vertical directions, wherein one of the holes 30 is oriented downwards while the other is oriented upwards. In this way, a pressurizing fluid may be introduced through one of the holes 30 oriented generally vertically downwards when positioned in a pipe 12 and another of the holes 30 oriented generally vertically upwards may be used to vent the pipe during the filling procedure. As will be understood by persons skilled in the art, the pressurizing fluid, when introduced into the pipe 12, will cause the contained air (or gases etc.) to rise vertically. Thus, having at least one of the holes 30 positioned at the upper end of the back plate 14 (when in use in a pipe) facilitates the venting procedure. The filling and venting process may be continued until the pressurizing fluid begins to exit from the upwardly oriented hole 30, which would indicate that the pipe 12 is completely filled with the pressurizing fluid, and indicating that the pressurizing step may continue. In the above description, reference has been made to "vertically upwards" and "vertically downwards". However, it will be understood that such orientation of the second holes 30 occurs when the back plate 14 is installed in a pipe when the apparatus of the invention is in use. It will also be understood that while having the second holes 30 being provided in opposite directions is preferred, the invention would function generally in the manner indicated above even where the second holes 30 are not exactly in the aforementioned orientations. In other words, various modifications can be made to the specific positioning of the second holes 30 while still achieving the desired result. Furthermore, while two second holes 30 and associated first holes 23 may be preferred (to provide two ports for filling and venting the pipe, accordingly), it will be understood that more than two of such holes may also be provided.

The ports or fluid passages formed by the first holes 23 and second, radial holes 30 (for convenience the combination of the first holes 23 and second holes 30 will be referred to as the ports or fluid passages 23) allow for fluid communication through the back plate 14 into the lumen of the pipe 12, when the apparatus is in use. It will be understood that for such communication, and for the placement of the back plate 14 within the pipe 12, the outer diameter of the back plate 14 would be preferably less than the inner diameter of the pipe 12. Thus, the ports 23, preferably including the couplings 24, may be used to pressurize, vent and/or monitor the lumen of the pipe 12 during the use of the apparatus 10. For this purpose, the ports 23 are preferably connected to any desired hoses, conduits, gauges and the like. It will be understood that the couplings 24, where provided, may facilitate such connection. It will also be understood that, while the outer diameter of the back plate 14 is chosen to be less (or slightly less) than the inner diameter of the pipe 12 so as to allow the ports to function (i.e. to allow fluid to pass through the second holes 30), the back plate 14 will still have a sufficiently large outer diameter to allow the sealing member 18 to function. That is, as will be appreciated by persons skilled in the art, if the back plate 14 is of too small an outer diameter, the clearance between the back plate 14 and the inner surface of the pipe 12 would not be sufficient to allow the sealing member 18 to be deformed and would therefore not result in the required seal between the back plate and the inner surface of the pipe. The limitations of the outer diameter of the back plate would be known to persons skilled in the art. For example, such determination may be made by calculating the deformed outer diameter of the sealing member 18.

The above mentioned holes 23 and 30 comprise one embodiment of the invention. It will be understood that in other embodiments, the radial second holes 30 may be omitted by providing first holes 23 that extend through the width of the back plate 14. In such way, the aforementioned fluid communication through the back plate 14 is provided. In such case, the first holes 23 may be provided very close to the outer diameter of the back plate 14 so as to achieve the preferred filling/venting function discussed above with respect to the second holes 30.

The back plate 14 may also be provided with a generally centrally located opening or thru-hole 26, which is adapted to be connected to a hose, conduit or the like. The thru-hole 26 may be used to facilitate one or more of the pressurization, venting and/or monitoring functions relating to the interior of the pipe 12, as will be described further below. In a preferred embodiment, the thru-hole 26 includes a coupling 28 that is secured thereto (such as be welding etc.), which serves to facilitate connection of the thru-hole 26 to the hose, conduit etc. mentioned above.

In one aspect, the back plate 14 may optionally be provided with a number of threaded, or tapped openings 32, provided radially inwardly on the outer perimeter thereof.

As shown in FIG. 3, the back plate 14 is, one embodiment, provided with two openings 32, provided at one end thereof and circumferentially separated from each other. The openings 32 are adapted to receive bolts or screws or the like, such as, by way of example only, button head cap screws (BHCSs) that aid in positioning the back plate 14 when being installed within a pipe. Specifically, the BHCSs are used as legs to support the back plate 14 as it is inserted into the pipe. As will be understood, the use of screws, such as BHCSs, avoids direct contact between the outer edge, or perimeter of the back plate 14 and the inner surface of the pipe, thereby facilitating movement of the back plate 14 within the pipe. Further, the use of screws such as BHCSs, which have a rounded (or "button"-like) head, also facilitate the positioning of the back plate 14. As will be understood, particularly where the apparatus of the invention is used with large diameter pipes, each component forming the apparatus, in particular the solid back plate 14, would be fairly heavy. As such, the use of positioning aids such as BHCSs and the like facilitates the installation of the apparatus when used in a pipe. It will also be understood that such positioning aids or bolts are optional and that any similar type of device or devices may be used.

As shown in FIG. 1, the apparatus 10 also includes a first or inner compression ring 34 and an associated first or inner gripper ring 36. As discussed below, and as illustrated in FIG. 1, the combination of the compression ring 34 and gripper ring 36 result in the gripper ring 36 frictionally engaging, or "gripping" the inner surface of the pipe 12. The first compression ring 34 is shown in more detail in FIGS. 7 to 9. The first gripper ring 36 is shown in more detail in FIGS. 10 to 13. As shown in FIG. 1, the first compression ring 34 is initially positioned distally from the pipe 12 opening, when the apparatus is in use, as compared to the first gripper ring 36.

Both the first compression ring 34 and the first gripper ring 36 are preferably generally annularly shaped bodies, each having an inner diameter and an outer diameter. As shown in FIG. 1, the outer diameters of both the first compression ring 34 and the first gripper ring 36 are sized to be inserted within the pipe 12 and axially aligned therewith. The outer diameter of the first compression ring 34 comprises a beveled edge 38, whereby the compression ring 34 is provided with an outer diameter that tapers from one end of the compression ring 34 to the other. When positioned in a pipe 12, the first compression ring 34 is arranged such that smaller outer diameter is positioned proximal to the pipe 12 opening, as shown in FIG. 1. As shown, for example, in FIGS. 7 and 8, the first compression ring 34 does not necessarily have an inner "diameter" per se but does have an inner opening of an irregular shape. It will therefore be understood that the term "inner diameter" as used in this context is for convenience and is not intended to limit the shape of the first compression ring 34 in any way. As will be understood from the present disclosure, the first compression ring 34 is preferably designed to have an inner opening of some nature.

The first gripper ring 36 has an inner diameter having a bevel or taper 40, which is adapted to cooperate with the outer beveled edge 38 of the first compression ring 34 when the apparatus is in use. The bevel 40 of the first gripper ring 36 results in the gripper ring 36 having a gradually increasing inner diameter from one end of the ring 36 to the other. When in the installed position, the first gripper ring 36 is arranged so that the smaller inner diameter is positioned proximal to the opening of the pipe 12. The outer diameter of the first gripper ring is generally constant and is sized to fit within the pipe 12.

FIG. 1, illustrates the arrangement of the first compression ring 34 and the first gripper ring 36 when the apparatus is in use. As shown, the inner diameter bevel 40 of the first gripper ring is oppositely directed from the beveled outer edge 38 of the first compression ring when the apparatus is installed. In this arrangement, the oppositely oriented bevels serve to form a ramp to drive the first gripper ring 36 radially outwardly to frictionally engage the inner surface of the pipe 12. That is, as will be understood by persons skilled in the art, as the first compression ring 34 and the first gripper ring 36 are axially moved towards each other, the oppositely directed bevels, 38 and 40, result in the first gripper ring being subjected to a radially outward or expansive force, thereby forcing the outer diameter of the first gripper ring 36 against the inner surface of the pipe 12. In one embodiment of the invention, as illustrated in the figures, the bevels 38 and 40 may be of the same slope. However, in other embodiments, the respective slopes of the bevels 38 and 40 may be different. The relative arrangement of the bevels will be apparent to persons skilled in the art with the aim of causing the first compression ring 34 to cause radially outward movement or deformation of the first gripper ring 36.

Figure 10:
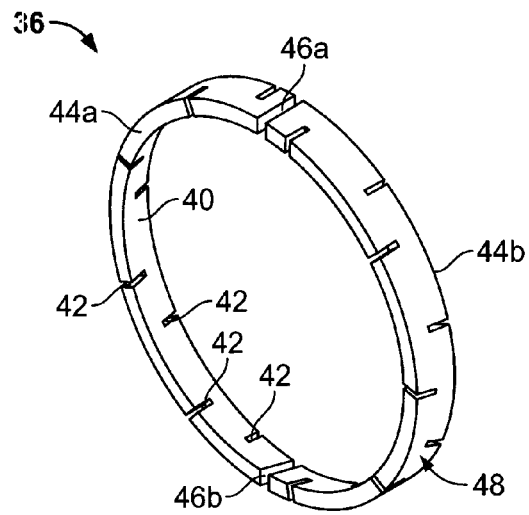
FIG. 10 is a perspective view of a first or inner gripper ring according to an aspect of the invention.
Figure 11:
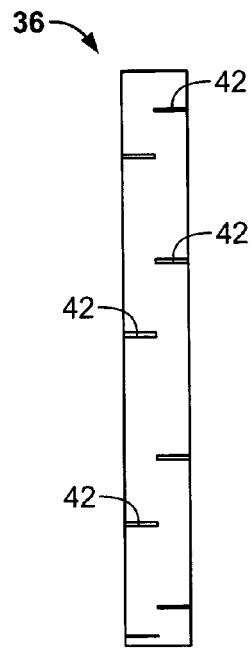
FIG. 11 is a side view of the first gripper ring shown in FIG. 10.
Figure 12:
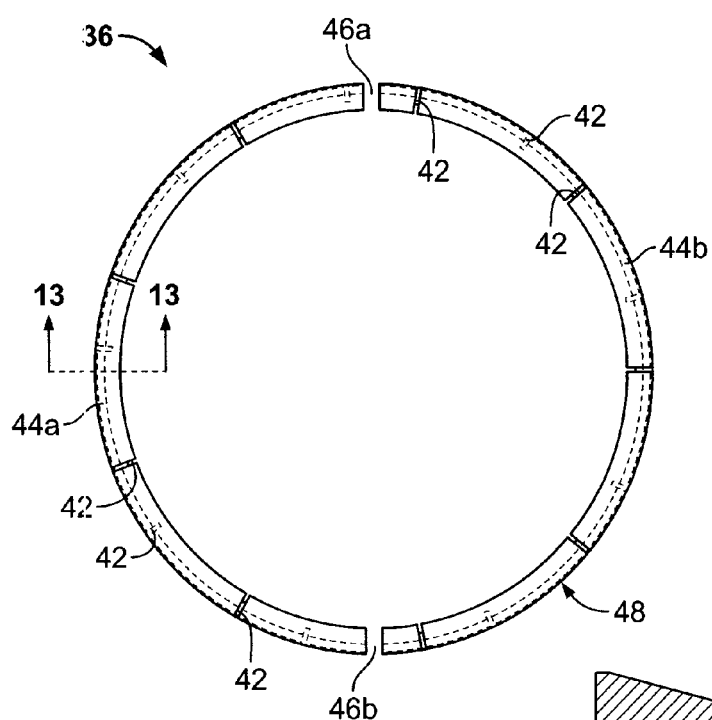
FIG. 12 is a front view of the first gripper ring shown in FIG. 10.

To ensure that the first gripper ring 36 is radially outwardly deflected, as opposed to a radially inward deflection of the first compression ring 34, the first compression ring 34 is preferably designed with a greater tensile strength. For example, in the embodiment illustrated in the figures (e.g. FIGS. 1 and 7), the first compression ring 34 may be designed with greater mass as compared to the first gripper ring 36 to result in the required tensile strength. Alternatively, the first compression ring 34 may be made of a different, stronger material as compared to the first gripper ring 36 to achieve the same result. As a further alternative, or to further ensure that the first gripper ring 36 is radially outwardly deformed or expanded, the first gripper ring 36 is preferably provided with a series of cuts 42 that partially extend through the gripper ring 36. As illustrated in FIGS. 10 to 12, and in accordance with a preferred embodiment of the invention, the first gripper ring 36 includes a plurality of cuts 42 that extend from one end and generally about half way through the width of the ring 36 body. As also shown, the cuts 42 preferably extend from both ends but in a staggered, or alternating manner.

In another embodiment, as illustrated in FIGS. 10 and 11, the first gripper ring 36 may be provided in two or more sections. FIGS. 10 and 11 illustrate an embodiment of the invention wherein the first gripper ring 36 is provided in two sections comprising first and second sections 44a and 44b, respectively. When the first gripper ring 36 is formed, the first and second sections 44a, 44b are preferably separated by two slots 46a, 46b. In such manner, the separation offered by the slots 46a, 46b facilitates installation of the first gripper ring within the pipe 12. It will also be understood that providing the first gripper ring 36 in two sections also facilitates removal of the apparatus 10. That is, a one piece gripper ring 36 may be permanently deformed when expanded radially, in which case removal of same would be difficult. Thus, by having the gripper ring provided in two or more sections, each section may be easily removed from the pipe 12. Various other means for causing radial expansion of the first gripper ring 36 may be used with the apparatus of the invention.

It will be understood that the first gripper ring 36 is not restricted in design to the above described two-part structure. Various other alternative structures, including a single body, may be used in the invention.

Figure 13:
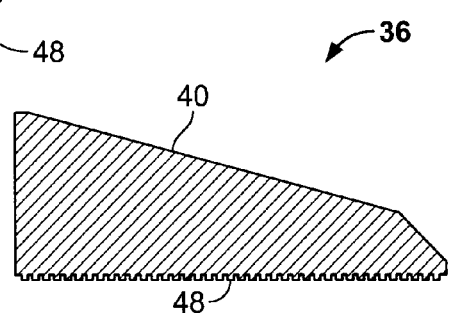
FIG. 13 is a side cross sectional view of a portion of the first gripper ring shown in FIG. 12, taken along the line A-A thereof.
Figure 14:
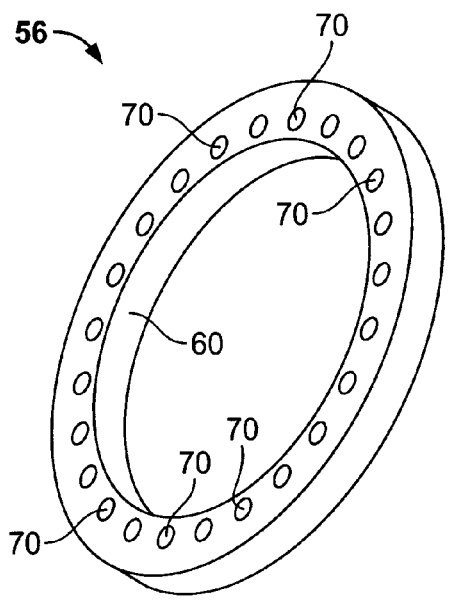
FIG. 14 is a perspective view of a second or outer compression ring according to an aspect of the invention.
Figure 15:
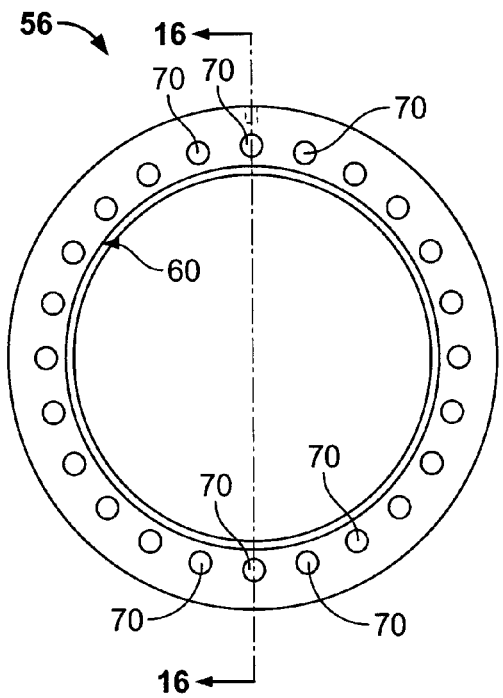
FIG. 15 is a front view of the second compression ring shown in FIG. 14.
Figure 16:
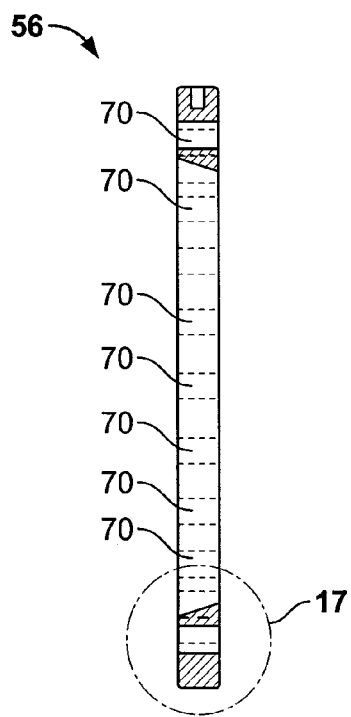
FIG. 16 is a side cross sectional view of the second compression ring shown in FIG. 15, taken along the line A-A thereof.
Figure 17:
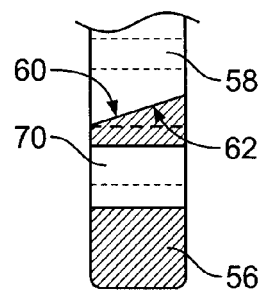
FIG. 17 is a partial side cross sectional view of the second compression ring as shown in FIG. 16, in combination with a second gripper ring.
Figure 18:
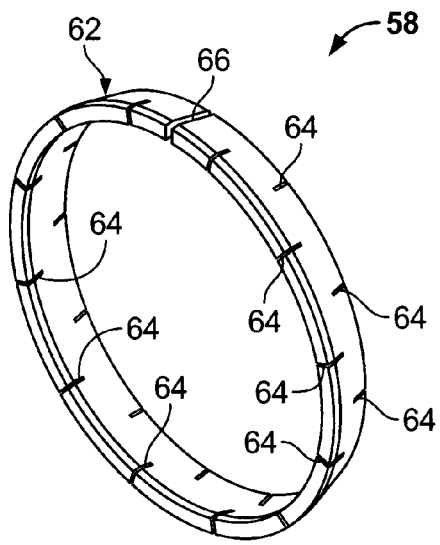
FIG. 18 is a perspective view of a second or outer gripper ring according to an aspect of the invention.
Figure 19:
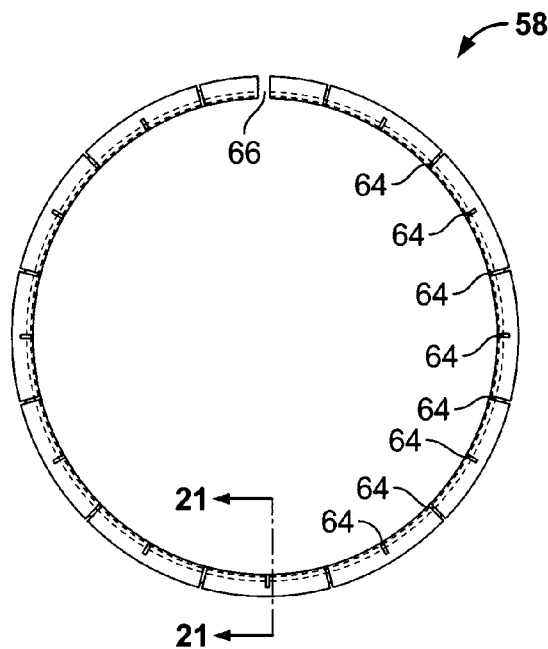
FIG. 19 is a front view of the second gripper ring shown in FIG. 18.
Figure 20:
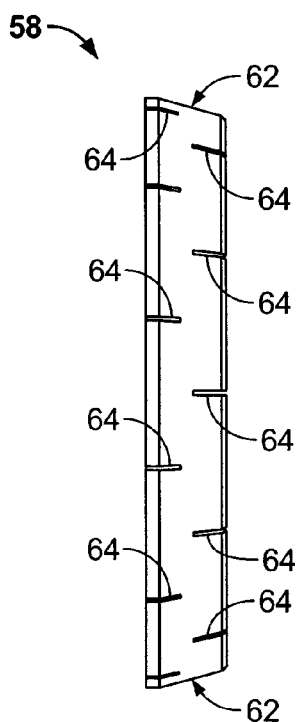
FIG. 20 is a side view of the second gripper ring shown in FIG. 18.

As shown in FIG. 13, the outer diameter of the first gripper ring 36 may preferably comprise a grooved 48 or other such textured or treated surface enhancement to further strengthen the frictional engagement between the gripper ring 36 and the inner surface of the pipe 12 when the apparatus is in use. It will be understood that such grooves 48 would be designed to not significantly damage the surface of the pipe 12.

Figure 9:
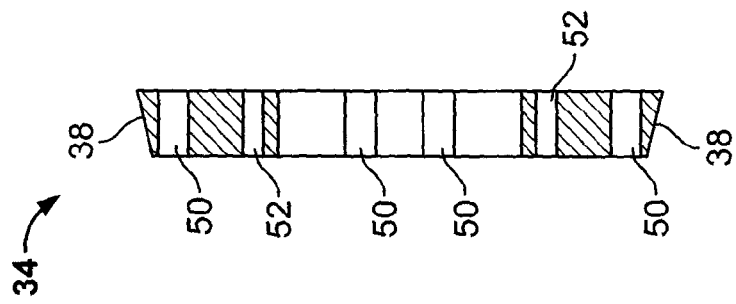
FIG. 9 is a side cross sectional view of the first compression ring shown in FIG. 8, taken along the line A-A thereof.

Referring again to FIGS. 7 to 9, the first compression ring 34 is shown to include a plurality of outer bolt holes 50 that are generally circumferentially equidistantly spaced. The bolt holes 50 are provided at a radius of the first compression ring 34 that corresponds to the positions of the threaded bolt holes 22 provided on the back plate 14. As shown in FIG. 9, the bolt holes 50 extend through the width of the first compression ring 34. As will be understood from the following description, the aforementioned first bolts (also discussed further below) for engaging the apparatus 10 will extend through the bolt holes 50 and engage the threaded bolt holes 22 of the back plate 14.

Figure 8:
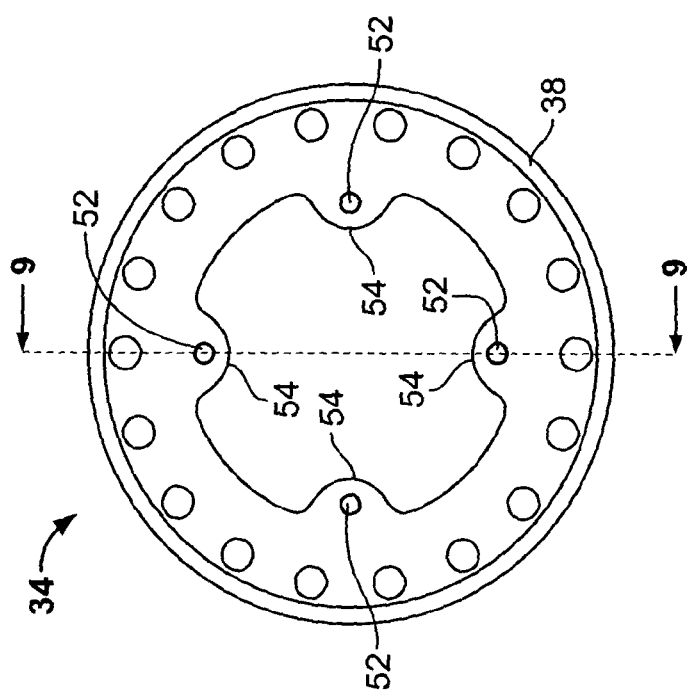
FIG. 8 is a front view of the first compression ring shown in FIG. 7.
Figure 7:
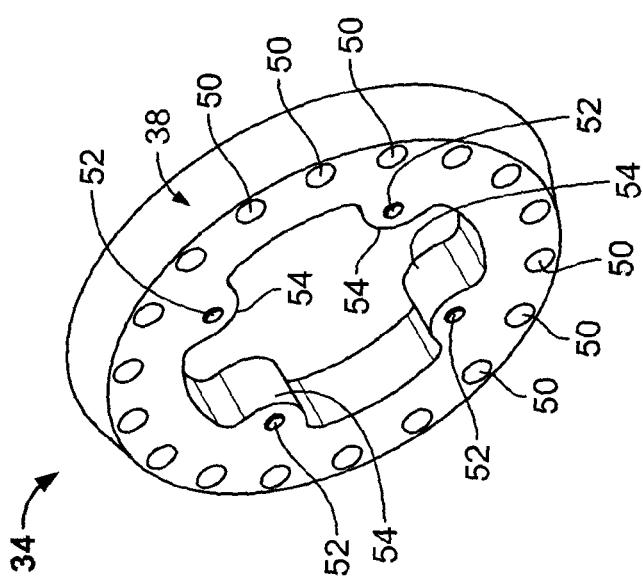
FIG. 7 is a perspective view of a first or inner compression ring according to an aspect of the invention.

As will be understood, due to the weight of the components of the apparatus of the invention, removal from within a pipe would be difficult without some means of grasping one or more components thereof. For this reason, one or more of components of the apparatus may optionally be provided with a means for extracting the apparatus of the invention from a pipe after the sealing operation has concluded. In one example as illustrated in FIGS. 7 to 9, such means of assisting the extraction comprises a number of further, inner bolt holes 52 that are provided generally circumferentially equidistantly on the first compression ring 34, but at a radius that is less than that of the outer bolt holes 50. In the example shown in FIGS. 7 to 9, it is noted that four inner bolt holes 52 are provided on the first compression ring 34. However, it will be appreciated that the number of such bolt holes 52 can be varied based on the size and/or weight of the first compression ring 34. The inner bolt holes 52 may be provided at a location close to the inner diameter of the first compression ring 34. However, as an alternative, and as shown in FIGS. 7 and 8, the first compression ring 34 may be provided with a number of radially inwardly directed projections 54 to accommodate the inner bolt holes 52. In the embodiment illustrated in FIGS. 7 to 9, the inner bolt holes 52 on the first compression ring 34 are threaded so as to accommodate bolts or the like therein, which also comprise the above noted means for extracting the apparatus. In particular, such bolts would preferably comprise eye bolts that can be screwed into the inner bolt holes 52 when the apparatus needs to be extracted from a pipe (or at any time), which allows a chain, rope or any other such device(s) to be connected to such bolts so as to allow the apparatus to be pulled towards the opening of the pipe. It will be understood that although the use of the above described means for extracting has been defined in terms of removing the apparatus from the pipe, it can similarly be used to assist in positioning the apparatus within the pipe. It will also be understood that the aforementioned bolts (e.g. eye bolts) may be permanently secured to the first compression ring 34, if necessary, or provided, permanently or otherwise, on any other component of the apparatus.

FIG. 1 also illustrates the second or outer compression ring 56 and the second or outer gripper ring 58 of the apparatus 10. As shown, the arrangement of the second compression ring 56 and second gripper ring 58 is the opposite of that described above with respect to the first compression ring 34 and first gripper ring 36. This is primarily due to the fact that the second compression ring 56 and second gripper ring 58 are arranged to grip the outer surface of the pipe 12. As discussed above, the first gripper ring 36 is adapted to be forced over the first compression ring 34, whereby the first compression ring 34 forces the first gripper ring 36 radially outwardly within the pipe 12, when the apparatus 10 is in use, to cause the first gripper ring 36 to frictionally engage the inner surface of the pipe 12. In an opposite manner, the second compression ring 56 is designed to pass over the second gripper ring 58, when the apparatus 10 is in use. As will be understood, this forces the second gripper ring 58 radially inwardly whereby the second gripper ring frictionally engages the outer surface of the pipe 12.

The second or outer compression ring 56 is illustrated in more detail in FIGS. 14 to 17. As shown in FIGS. 1 and 14 to 17, the second compression ring 56 comprises a generally annular ring structure having an inner diameter that is beveled 60. Such bevel 60 results in the second compression ring having a lower inner diameter at one end, which gradually increases when moving towards the opposite end. As shown in FIG. 1, when the apparatus 10 is in use, the second compression ring 56 is arranged so that the larger inner diameter thereof is positioned proximal to the opening of the pipe 12.

The second or outer gripper ring 58 is illustrated in more detail in FIGS. 18 to 21. As shown, the second gripper ring 58 has an outer edge or diameter 62 that comprises a bevel, whereby, the outer diameter of the second gripper ring 58 tapers or gradually reduces from one end to the opposite end. When the apparatus 10 is installed on a pipe 12, as shown in FIG. 1, the second gripper ring 58 is arranged so that the larger out diameter end is positioned proximal to the pipe 12 opening.

As illustrated in FIG. 1, when the apparatus is in use, the second compression ring 56 and second gripper ring 58 are arranged on a pipe, so that the second compression ring is distal to the opening of the pipe. In this arrangement it will be seen that as the second compression ring 56 and second gripper ring 58 are urged towards each other in the axial direction, the beveled inner diameter of the second compression ring 56 is driven over the beveled or tapered outer diameter of the second gripper ring 58, thereby causing the second gripper ring 58 to be radially compressed against the outer surface of the pipe 12. In other words, as with the first compressing ring 34 and first gripper ring 36 discussed above, the oppositely directed bevels of the second compression ring 56 and second gripper ring 58 form a ramp to drive the second gripper ring 58 radially inwardly to frictionally engage the outer surface of the pipe 12.

As with the first compression ring 34 and first gripper ring 36 discussed above, the second compression ring 56 and second gripper ring 58 are preferably designed so as to ensure that the second gripper ring 58 is compressed as opposed to causing radial expansion of the second compression ring 56. For example, as discussed above, in a preferred embodiment, the second compression ring 56 will be designed to have greater mass or rigidity as compared to the second gripper ring 58. Further, in a preferred embodiment as illustrated in FIGS. 18 to 21, the second gripper ring 58 may be provided with a plurality of cuts 64 extending axially from one or both ends towards the center of the ring 58. As will be understood, such cuts 64 serve to reduce the rigidity of the gripper ring. In addition, the second gripper ring 58 is preferably provided with a slot 66 extending axially through the width of the gripper ring 58. As will be understood, the slot 66 allows the second gripper ring 58 to be expanded and slid onto the outer surface of the pipe 12 when the apparatus is installed. When the apparatus is dismantled, the second gripper ring 58 may then be more easily removed off the pipe 12 by expanding same radially outwards. Various other means for causing radial compression of the second gripper ring 58 may be used with the apparatus of the invention.

Figure 21:
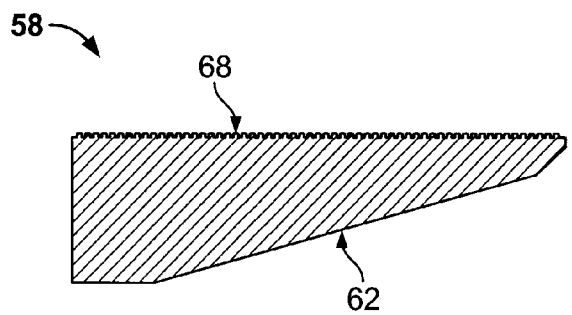
FIG. 21 is a side cross sectional view of a portion of the second gripper ring shown in FIG. 19, taken along the line A-A thereof.
Figures 22, 23, 24:
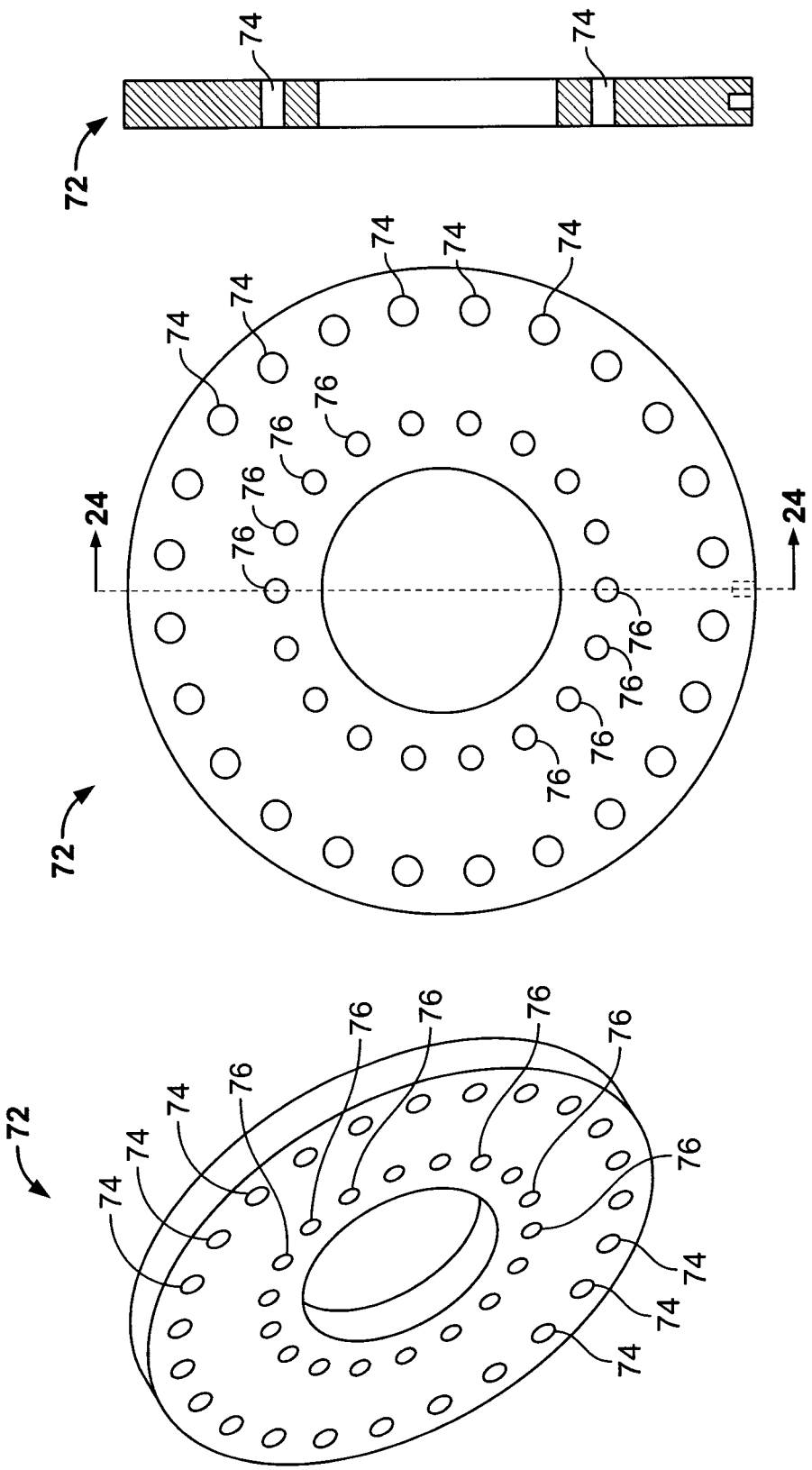
FIG. 22 is a perspective view of a front plate according to an aspect of the invention.
FIG. 23 is a front view of the front plate shown in FIG. 22.
FIG. 24 is a side cross sectional view of the front plate shown in FIG. 23, taken along the line A-A thereof.

The second gripper ring 58 may also be adapted to increase frictional engagement with the pipe 12. For example, as discussed above, the inner diameter of the second gripper ring 58 may be provided with grooves 68, as shown in FIG. 21, or some other textured or treated surface, which enhances the frictional engagement between the second gripper ring 58 and the outer surface of the pipe 12. It will be understood that such grooves 68 would be designed to not significantly damage the surface of the pipe 12.

Returning to FIGS. 14 to 17, it is noted that the second compression ring 56 is provided with a plurality of bolt holes 70 that extend axially through the width of the compression ring 56. The bolt holes 70 are circumferentially equidistantly spaced and are adapted to receive second bolts (shown as 92 in FIG. 31). The significance of the bolt holes 70 is discussed below.

FIGS. 1 and 22 to 24 illustrate a front, or sealing plate 72 of the apparatus 10. The front plate 72 comprises the opposite end of the apparatus 10 from the back plate 14. In a preferred embodiment, as illustrated in the figures, the front plate 72 comprises a generally annular disc having an outer diameter and an inner diameter. The outer diameter of the front plate 72 is designed to be greater than the outer diameter of the pipe 12 so as to allow a sufficient clearance there-between. Further, the inner diameter of the front plate 72 is designed to be smaller than the inner diameter of the pipe 12. In this way, the annular front, or sealing plate 72 covers the edge of the pipe 12 at the open end thereof. The front plate 72 includes two series of bolt holes, each of such series comprising a plurality of circumferentially equidistantly spaced. A first series of bolt holes 74 is provided near the outer diameter of the front plate 72 and the second series of bolt holes 76 is provided near the inner diameter of the front plate 72. The first series of bolt holes 74 are positioned to be aligned with the bolt holes 70 provided on the second compression ring 56. The second series of bolt holes 76 are positioned to be aligned with bolt holes 50 of the first compression ring 34 and the bolt holes 22 of the back plate 14.

Thus, as will be understood, the apparatus 10 of the invention may be divided into two sub-assemblies, namely, an inner sub-assembly, comprising the back plate 14 (including the sealing member 18), the first compression ring 34 and the first gripper ring 36; and an outer sub-assembly, comprising the second compression ring 56 and the second gripper ring 58.

As shown in FIG. 1, the front plate 72 is adapted to be pressed against the open end of the pipe 12. The front plate 72 may therefore optionally be provided with a groove or recess to accommodate the opening of the pipe 12 therein. Such groove or recess may optionally be provided with a sealing means to further seal the end of the pipe 12.

As discussed above, while the back plate 14 is, in one embodiment, a generally solid disc that prevents direct fluid communication between the interior of the pipe 12 on both sides thereof (i.e. the back plate 14, when in use, seals the portion of the pipe interior on the second side 15 thereof), all other components of the invention have inner diameters or openings. Thus, in such arrangement, the opening 26 and/or the ports 23 (i.e. inclusive of the first holes 23 and the second holes 30) provided on the back plate 14 are accessible through the front plate 72. As mentioned above, the opening 26 and/or the holes 23, preferably include respective couplings 28 and 24. In one aspect, the pipe 12 being tested may be pressurized by introducing a pressurizing fluid through one or more of the opening 26 or holes 23. Such elements would also be used to vent and/or monitor the interior volume of the pipe 12. Pressurization of the pipe 12 allows for pressure testing to test the integrity of the pipe and/or one or more welds provided thereon. For example the pipe 12 may be formed of two or more segments or may include a valve, flange or other such equipment welded thereon. As discussed above, the testing of such welds is important. In use, the apparatus 10 of the invention allows the interior of the pipe 12 to be pressurized after the apparatus is installed. Preferably after venting any air within the pipe 12 (i.e. to remove any compressible gases), the pressure within the pipe 12 may then be monitored, wherein a drop in pressure signifies a weld or joint etc. that lacks the sufficient integrity.

In some situations, the pipe 12 may be open at more than one end. In such cases, more than one of the above discussed apparatuses may be used to seal both (or all of) the pipe openings. In such case, it will be understood that the pressurizing and venting procedures may be conducted through one or more of the apparatuses.

One of the advantages offered by the apparatus of the present invention over that of know pressure testing devices is that, in addition to sealing an end of a pipe, the apparatus also frictionally engages both the inner and outer surfaces of the pipe that is sealed. This feature results in the apparatus being effectively secured to the pipe and avoids the seal from being dislodged once the pipe is pressurized. As will be understood, the pressure testing of pipes is conducted at very high pressures and, as such, any dislodging of the sealing apparatus would result in a highly dangerous situation where the sealing apparatus may be explosively "shot out" from the pipe.

Another advantage of the apparatus of the invention can be seen in FIG. 1. Due to the installed arrangement of the back plate 14 and the first compression ring 34 and first gripper ring 36, it will be seen that as the pressure distal (i.e. away from the opening of the pipe 12) builds within the pipe, the pressure serves to force the back plate 14 towards the pipe opening. In the result, the back plate 14 urges the first compressing ring 34 further against the first gripper ring 36, which further increases the gripping or frictional force between the apparatus 10 and the inner surface of the pipe 12. As will be appreciated, this results in the first compression ring 34 being maintained in position within the pipe 12. In addition, due to the back plate 14 being forced against the immobilized first compression ring 34, the sealing member 18 is further compressed between the back plate 14 and the first compression ring 34. This therefore results in an increased seal being formed between the apparatus 10 and the inner surface of the pipe 12.

The method of the invention will now be described with reference to the apparatus 10 discussed above. In general, the method of the invention comprises sealing or closing at least one end of a pipe 12 that is to be pressure tested. Such testing can, for example, be for the purposes of testing the integrity of one or more weld on the pipe 12. The step of sealing comprises the formation of a circumferential seal with the inner surface of the pipe 12 to be tested and the closure of the lumen of the pipe 12 at a location close to the opening of the pipe. The apparatus also frictionally engages the inner and outer surfaces of pipe 12 so as to prevent relative axial movement between the apparatus 10 and the pipe 12. The method also comprises, in one aspect, using one or more similar apparatuses 10 to seal an opposite end of the pipe 12 if needed (i.e. in situations where the pipe is open on both ends) or other openings in such pipe. The invention is not limited to the number of openings in the pipe. Once the seal or seals are formed at the one or more openings thereof the interior of the pipe is pressurized and the pressure monitored. If the pressure is maintained, the integrity of the pipe 12 and/or welds is verified. Any drop in the pressure within the pipe 12 signifies a failure in the pipe's integrity and/or that of at least one of the welds thereon.

As would be apparent from FIG. 1, in a first step, the inner and outer sub-assemblies of the apparatus 10 are positioned in and on the pipe 12, respectively, at a location generally close to the opening of the pipe 12 that is to be sealed. In one aspect of the method, the inner sub-assembly is installed first followed by the outer sub-assembly. However, it will be understood that the order of installation can easily be reversed. Thus, in one aspect, the back plate 14, with the sealing member 18, may be first inserted into the pipe 12, followed by the first compression ring 34 and then the first gripper ring 36. As discussed above, the back plate 14 is preferably positioned and rotated (if necessary) within the pipe 12 so that the second holes 30 are oriented vertically away from each other. In situations where devices such as cap screws or the like are provided in the openings 32, it will be understood that the second holes 30 would be pre-determined and, therefore, rotation of the back plate 14 for positioning the second holes 30 would not be necessary.

As mentioned above, the first gripper ring 36 may be provided in one or more sections. Similarly, the second compression ring 56 is provided over the outer surface of the pipe 12, followed by the second gripper ring 58. Next the front plate 72 is positioned against the open end of the pipe 12. A plurality of second bolts (discussed further below as element number 92 shown in FIG. 31)) is passed through the first series of bolt holes 74 of the front plate 72 and through the bolt holes 70 of the second compression ring 56. First nuts are then provided and tightened so as to urge the second compression ring 56 axially towards the front plate 72. In a preferred aspect, the front plate 72 is maintained pressed against the opening of the pipe 12 and, therefore, the tightening of the first nuts on the second bolts (element 92 as shown in FIG. 31) results in the second compression ring 56 being moved towards the front plate 72.

Figure 31:
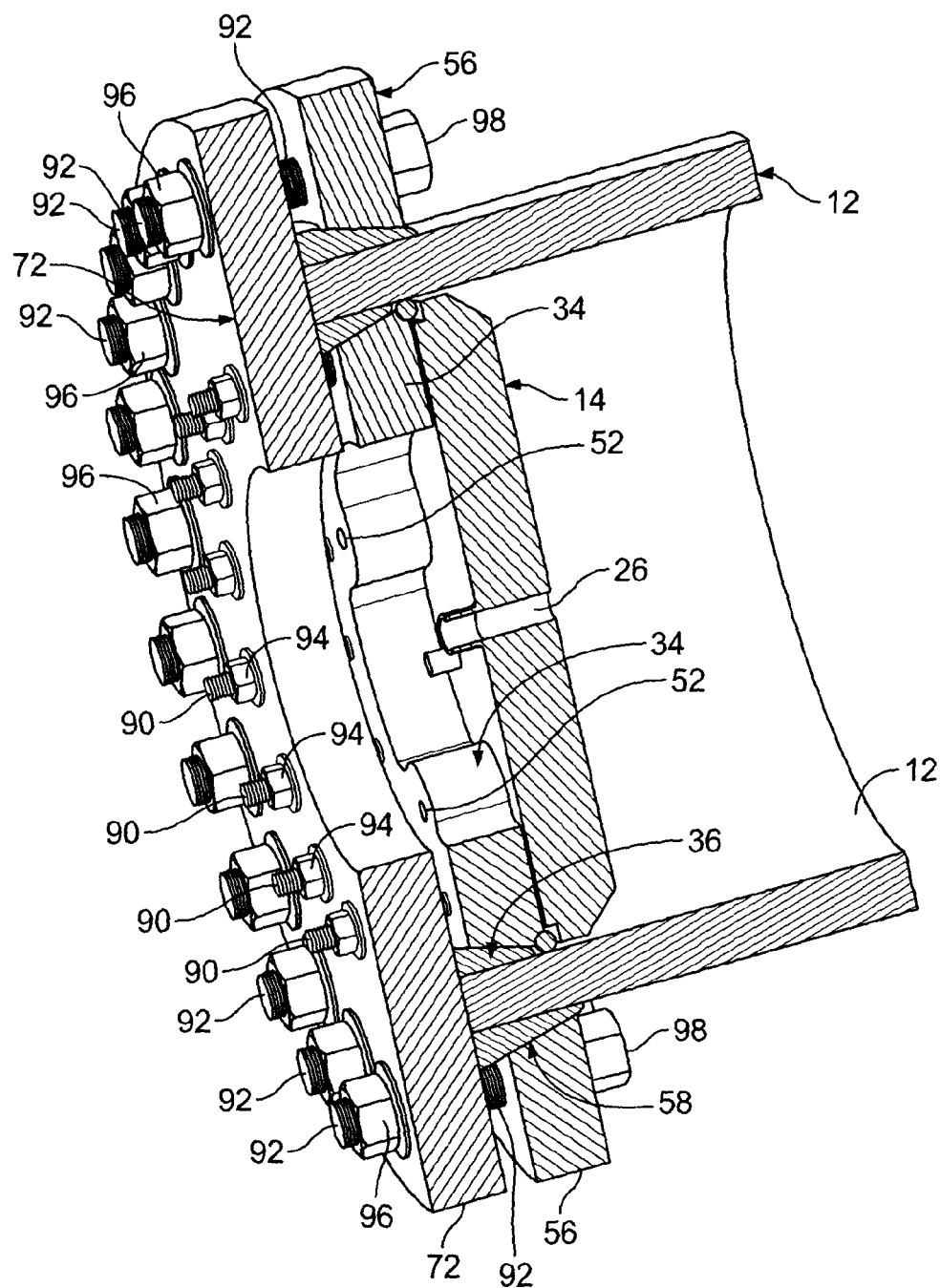
FIG. 31 is a cross sectional perspective view of the apparatus shown in FIG. 1, according to another embodiment illustrating the bolts used to connect the apparatus.

Similarly, first bolts (element 90 as shown in FIG. 31) are passed through the second series of bolt holes 76 of the front plate 72. The first bolts are also extended through the bolt holes 50 of the first compression ring 34 and into the threaded bolt holes 22 of the back plate 14. Tightening of the first bolts into the back plate 14 results in the back plate 14 being urged axially towards the front plate 72 (primarily due to the front plate being pressed against the open end of the pipe 12 and, therefore being immobilized). In this process, the back plate 14 is moved axially towards the opening and, in the result, causes similar movement of the first compression ring 34 against the first gripper ring 36. In the latter case, the lower outer diameter, proximal end of the first compression ring 34 is urged into the larger inner diameter, distal end of the first gripper ring 36, thereby resulting in the first gripper ring 36 being expanded radially outwardly. Such radial expansion results in the formation of a frictional engagement (i.e. "gripping") of the first gripper ring 36 with the inner surface of the pipe 12. As shown in FIG. 1, the axial movement of the first gripper ring 36 is impeded once contact is made with the front plate 72. Further tightening of the first bolts increases the frictional engagement between the first gripper ring 36 and the inner surface of the pipe 12. Concurrently, the axial movement of the back plate 14 against the first compression ring 34 results in compression of the sealing member 18. Due to the presence of the groove 16 on the back plate 14, the compression of the sealing member 18 forces it to be radially outwardly expanded against the inner surface of the pipe 12. In the result, the sealing member 18 forms a fluid tight circumferential seal with the inner surface of the pipe 12.

In the above description, reference is made to the use of first and second bolts that are extended through respective bolt holes. It will be understood that in some embodiments, one or both of the sets of bolts may be permanently secured to at least one of the aforementioned components, such as by welding etc. For example, the second bolts may be permanently attached to either the front plate 72 or the second compression ring 56, with nuts provided on the opposite ends thereof to cause the required axial advancement. Similarly, the first bolts may be permanently secured to the back plate 14 and allowed to extend through the bolt holes 76 provided on the front plate 72. Nuts would then be provided on the ends of the first bolts and tightened to urge the back plate 14 towards the front plate 72.

Although the use of bolts and associated nuts may be preferred, in other embodiments of the invention, other mechanical or hydraulic devices may also be used to achieve the desired result. For this reason, such bolts and the like may be generally referred to herein as means for urging.

As discussed above, once the two sub-assemblies of the apparatus 10 are positioned and installed, a pressurizing fluid is introduced into the lumen of the pipe 12 distal of the opening to pressurize the pipe 12. In one aspect, the pressurizing fluid may be introduced through one of the ports 23, and preferably via a coupling 24 associated therewith, where provided. The pressurizing fluid would be understood as being introduced through a hose or other such conduit (not shown) connected to one of the couplings 24. The other of the couplings 24 would preferably be connected to a vent hose or conduit (also not shown) so as to facilitate venting of any air etc. within the pipe during the pressurization step. As mentioned above, the holes 23 are preferably connected to radial holes 30, which extend through the outer diameter of the back plate 14. The pressure within the pipe would then be increased to the desired testing value and the pressure monitored as described above. For this step, the hose of conduit associated with one or both of the couplings 24 may include a pressure gauge or the like. However, in one aspect, any venting of monitoring of the pipe 12 may be accomplished, at least partially, using the opening 26 and the associated coupling 28, to which a separate vent hose or conduit and/or pressure monitoring means (i.e. pressure gauges and the like) may be attached. The hose or conduit may also be used to vent the interior of the pipe 12 either after the test is completed or during the pressurizing step. In one example, where two ends of a pipe are sealed according to the present invention, the pressurizing fluid comprising an inert gas or water etc. may be introduced at one end and any existing gases or vapors within the pipe may be vented through the other end. As discussed above, this filling/venting step is facilitated by positioning the back plate 14 within the pipe 12 being tested in such a manner so as to orient the second holes 30 vertically.

In the above description, the outer sub-assembly is described as being secured first onto the pipe 12. However, it will be understood that the inner sub-assembly may be secured first before the outer sub-assembly.

It will be understood that the inner sub-assembly (i.e. the back plate 14, first compression ring 34 and first gripper ring 36) and/or the outer sub-assembly (i.e. the second compression ring 56 and second gripper ring 58) may be loosely preassembled with the front plate prior to installation on the pipe 12. Such pre-assembly is possible since the frictional engagement with the pipe 12 is achieved upon tightening the respective nuts and/or bolts.

The apparatus and method of the present invention may be used on a large variety of sizes and thicknesses of pipes. Two examples are provided below where the apparatus is designed for use with a 20" schedule 120 pipe and a 36" schedule 80 pipe. Persons skilled in the art would appreciate the required modifications required for using the apparatus of the invention with other diameters and schedules of pipes.

Figure 25:
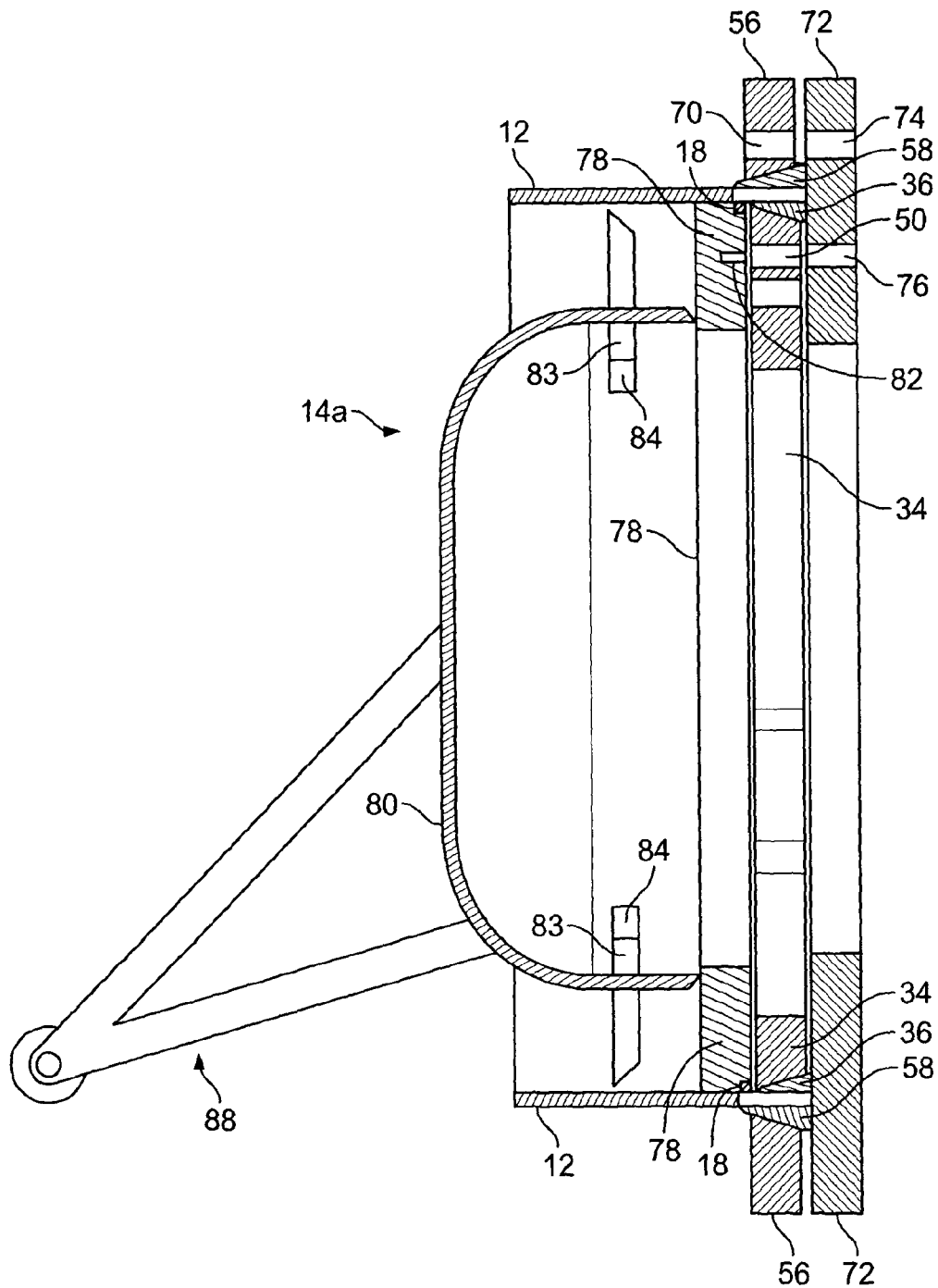
FIG. 25 is a schematic cross sectional view of an apparatus according to another aspect of the invention.
Figure 26:
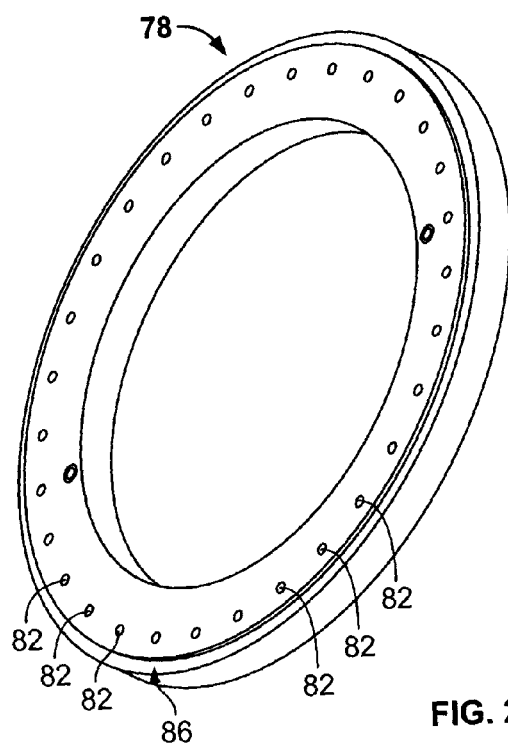
FIGS. 26 and 27 are front and rear perspective views, respectively, of the back plate ring as shown in FIG. 25.
Figure 27:
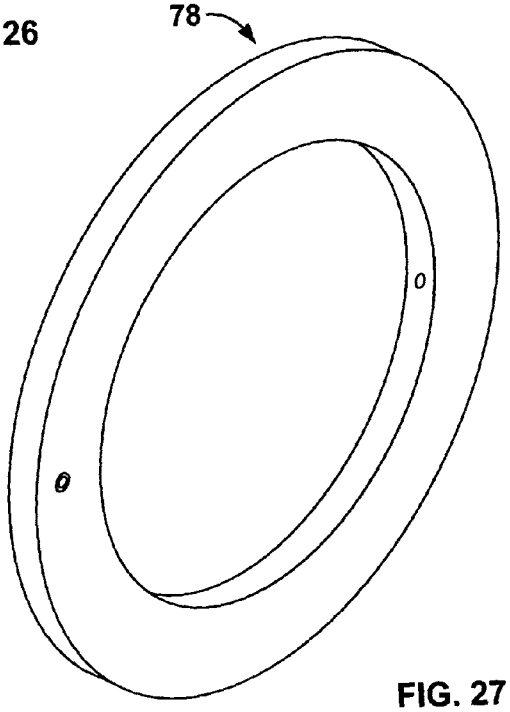
Figure 29:
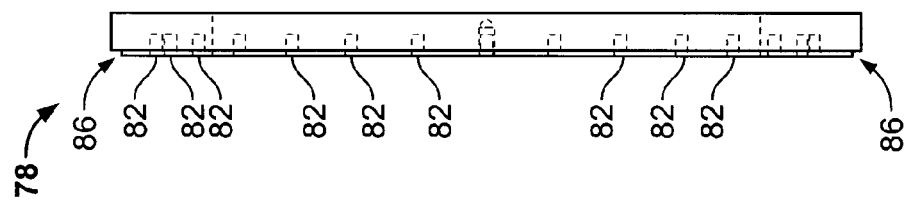
FIG. 29 is a side cross sectional view of the back plate ring shown in FIG. 28.
Figure 28:
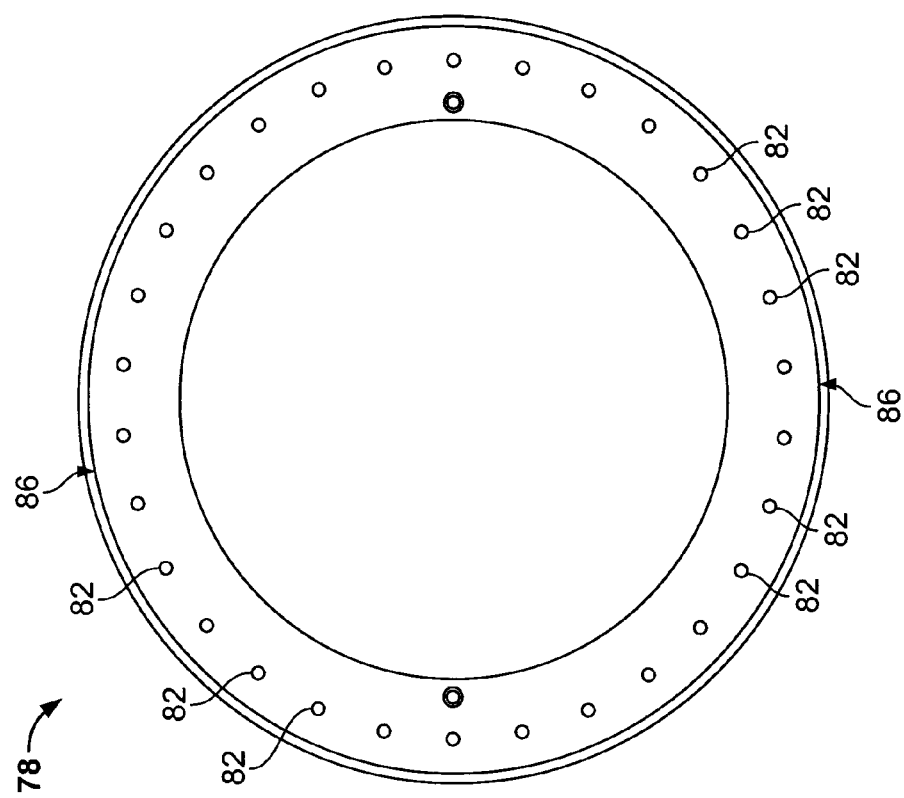
FIG. 28 is a front view of the back plate ring as shown in FIG. 26.

In cases where the pipe to be tested is of a large diameter, i.e. 36" or more, various structural modification may also be made to facilitate the installation and/or use of the apparatus of the invention. By way of example, an apparatus according an aspect of the invention, for use in large diameter pipes (for example, pipes having a diameter of 36" or more), is shown in FIG. 25, wherein elements that are similar to those described above are indicated with like reference numerals. As shown, the apparatus for use on larger sized pipes is very similar to that described above, with the exception of the previously described back plate 14 is replaced with a modified back plate shown at 14a. Specifically, with the embodiment shown in FIG. 25, the modified back plate 14a is comprised of a back plate ring 78 that is secured, such as by welding or other such means, to an associated "bell" shaped cap 80. As such, the singular term "back plate 14a" is used herein to refer to the combination of the back plate ring 78 and the cap 80. The back plate ring 78 is illustrated in more detail in FIGS. 26 to 29. As will be understood, the back plate ring 78 and cap 80 function in the same manner as the back plate 14 described above. However, due to its larger size, the combination of the back plate ring 78 and cap 80 serves to facilitate the manipulation of the back plate 14a and the installation of the apparatus within a pipe 12.

By replacing a solid disc back plate (such as illustrated by element 14 in previous figures) with a back plate 14a comprising a combination of a ring 78 and cap 80, a further advantage is realized. Specifically, in the case of large diameter pipes, a suitably sized back plate 14 will be needed. It will be understood that while such a solid disc back plate 14 would function in the manner described above, such element would have considerable weight and, therefore, would be difficult to manipulate, use and transport. For example, with "small" diameter pipes (i.e. pipes of approximately 20 inches in diameter or less), the thickness of the back plate may only need to be 3 inches. However, for pipes having a diameter of 24 to 36 inches or more, a solid back plate such as shown at 14 in previous figures, would need to be roughly 6 inches thick in order to withstand the pressures that would accumulate in the pipe 12 during the pressure testing phase. Thus, such a back plate would be very heavy.

However, by replacing the solid disc 14 with the modified back plate 14a, having the back plate ring 78 and cap 80 combination, a considerable weight reduction is realized. In such case, the ring 78 may only need to be 3 inches thick, with the cap 80 being even thinner. This is due to the orientation of the cap 80 and, specifically, the orientation of the convex side of the cap 80 facing within the pipe 12 (as shown in FIG. 25). In this orientation, as pressure accumulates within the pipe 12, force is applied to the cap 80 and, due to its "bell" shape, such force is distributed almost entirely to the outer edge thereof and against the ring 78. The body of the cap 80 would therefore not be deformed, despite it relatively thin structure, since its shape would be able to withstand such deformation, which would not be possible with a flat plate-like structure. Thus, with the modified back plate 14a having such ring 78 and cap 80 combination, a high pressure may be created within the pipe 12 without risking collapse of the back plate. Although the embodiment illustrated in FIG. 25 has been described in connection with "large" pipes, it will be understood that such embodiment may be used with any size of pipe. In any event, the combination of back plate ring 78 and cap 80 results in an apparatus that is easier to manipulate and transport due to its reduced weight.

As shown in FIGS. 25 to 29, the back plate ring 78 of the modified back plate 14a comprises a generally annular shaped disc having an outer diameter and an inner diameter. As with the back plate 14 previously described, the back plate ring 78 is provided with a plurality of threaded bolt holes 82 that are adapted to receive bolts, i.e. first bolts (discussed further below and shown as element 90 in FIG. 32), extending from the front plate 72 in the manner described above. As also mentioned above, the first bolts (shown as 90 in FIG. 32) may be permanently secured to the back plate ring 78.

The back plate ring 78 is also provided with a groove 86 or similar structure that is adapted to receive a sealing member 18, such as an O-ring or the like, in the same manner as described above.

The cap 80 is secured to the back plate ring 78 in any suitable manner, such as by welding or the like. It will be appreciated that the cap 80 is secured to the back plate ring 78 in a fluid tight manner so as to prevent passage of fluids, such as the aforementioned pressurizing fluid, through the joint between the cap 80 and the back plate ring 78.

The cap 80 is provided with two or more ports 83 that provide fluid communication between opposite sides of the cap 80. As shown in FIG. 25, the ports 83 extend through the cap 80 and, in a preferred embodiment, include couplings 84 that are adapted to connect to hoses or other such conduits in the same manner as described above with respect to couplings 24 of the back plate 14. As discussed above with respect to the second holes 30, in a preferred embodiment, the ports 83 are provided on opposite sides of the cap 80 so that, when the modified back plate 14a is positioned within a pipe, the ports 83 may be oriented vertically to facilitate the filling/venting step of the pipe as described above.

Figure 32:
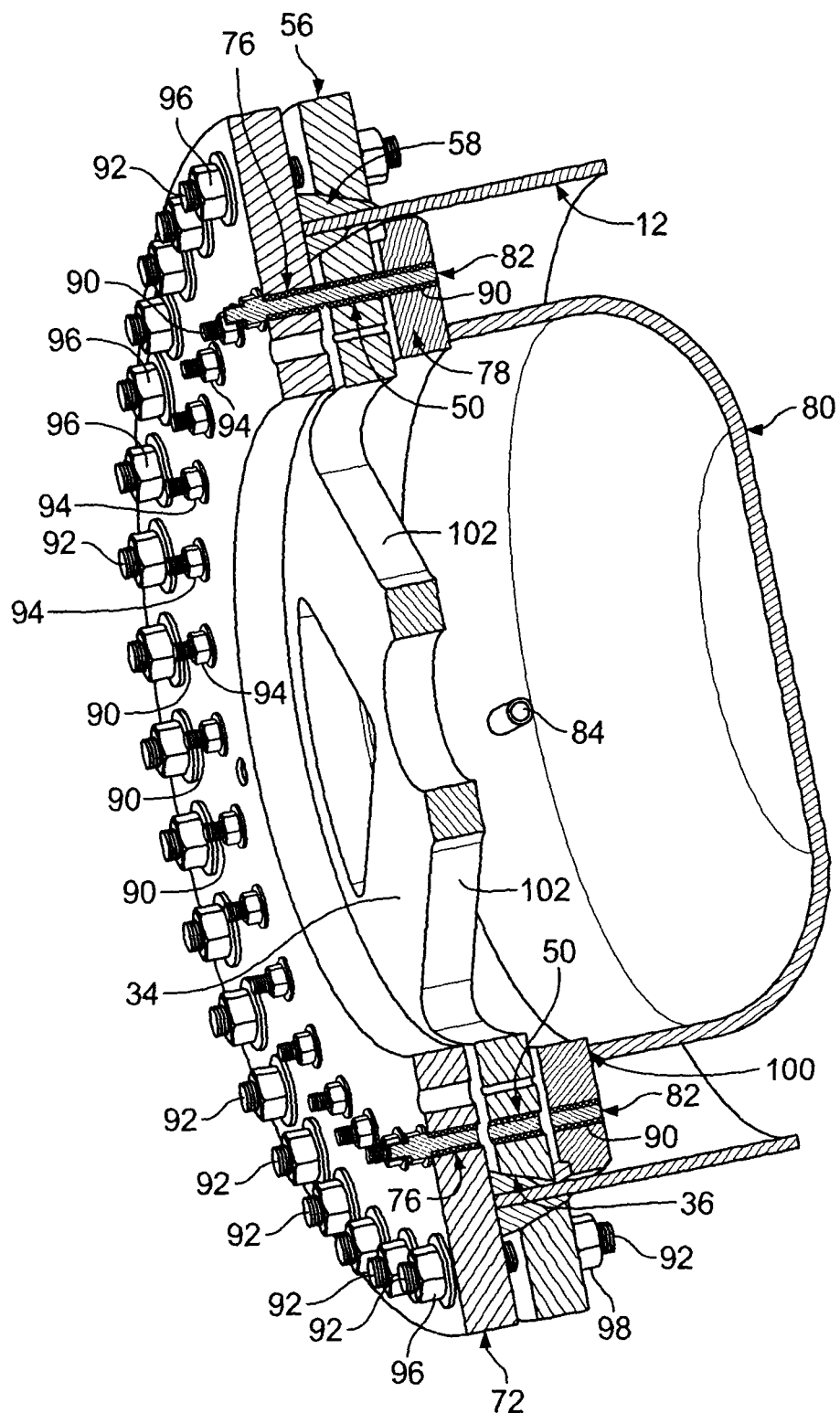
FIG. 32 is a cross sectional perspective view of the apparatus shown in FIG. 25 according to another embodiment.

FIG. 32 illustrates the above mentioned arrangement of ports 83 on the cap 80 when the apparatus, including the modified back plate 14a, is installed in a pipe 12. As shown, the ports 83 are provided generally on opposite ends of the cap 80 so that, when positioned in the pipe 12, the ports 83 are arranged vertically so that, as before, the lower oriented port 83 may be used to fill the pipe with a pressurizing fluid while the upwardly oriented port 83 can be used to vent the pipe 12 during the filling step.

In one embodiment, the cap 80 may be provided with a carriage apparatus such as that shown at 88, which serves to facilitate installation of the cap 80 and back plate ring 78 assembly within a pipe. As will be understood, the weight of the back plate ring 78 itself, for use in a 36 inch pipe, may exceed 250 lbs and, as such, any carriage means etc. would assist the manipulation of the apparatus when being installed in the pipe 12.

The operation or method of use of the apparatus shown in FIG. 25 would generally be the same as that described above.

FIG. 32 illustrates the embodiment of FIG. 25 with the first and second bolts included. As shown in FIG. 32, the first bolts 90 and second bolts 92 are provided through the front plate 72 in the same manner as described above. Thus, as shown, first bolts 90 extend through the bolt holes 76 of the front plate 72, through bolt holes 50 of the inner or first compression ring 34 and into bolt holes 82 of the back plate ring 78. As mentioned above, the first bolts 90 may be permanently secured to the back plate ring 78. Nuts 94 are used on the first bolts 90 in order to urge the back plate ring 78 and the front plate 72 together. The second bolts 92 are provided through bolt holes 74 of the front plate 72 and through bolt holes 74 of the second or outer compression ring 56. Nuts 96 and/or 98 are used on the second bolts 92 to urge the second compression ring 56 and the front plate 72 towards each other.

FIG. 32 also illustrates two other features of the subject embodiment of the invention. Specifically, FIG. 32 illustrates a weld 100 that secures the cap 80 to the back plate ring 78. In addition, FIG. 32 illustrates some additional structure of the first or inner compression ring 34. As shown, the first compression ring 34 may be provided with an inner diameter portion having a mesh-type structure that provides the first compression ring 34 with some rigidity and strength, while providing a reduced weight (as compared to a solid structure). In addition the members 102 forming the web structure may be used to remove the apparatus from the pipe 12.

Figure 33:
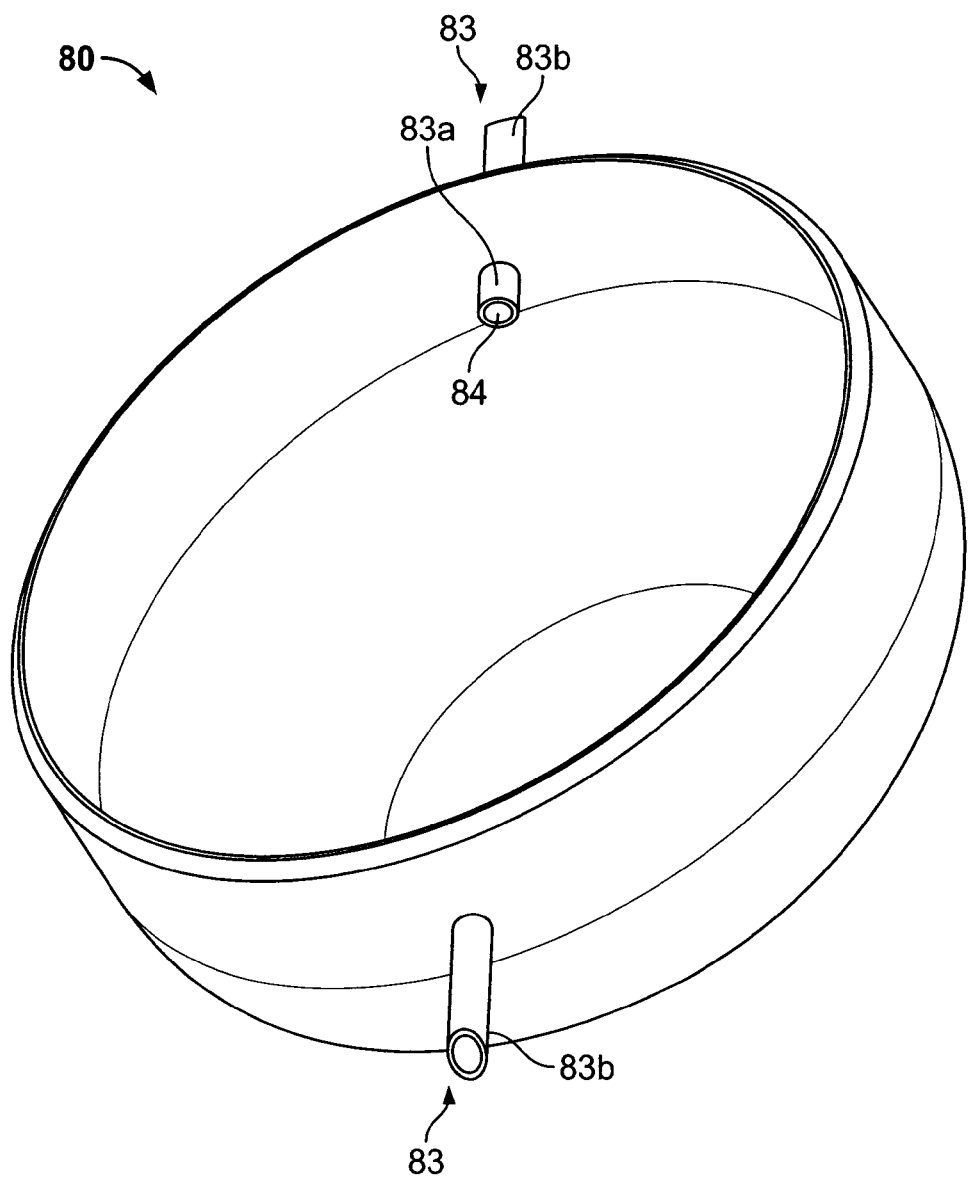
FIG. 33 is a front view of the cap of FIG. 25 or 32 in isolation.

FIG. 33 illustrates the cap 80 in isolation and further illustrates the ports 83 provided thereon. As shown, the ports 83 include an internal stem 83a and an external stem 83b. The internal stem 83a may be provided with couplings 84 to facilitate connection to a hose or the like. The external stem 83b protrudes into the lumen of the pipe (not shown).

Figure 34:
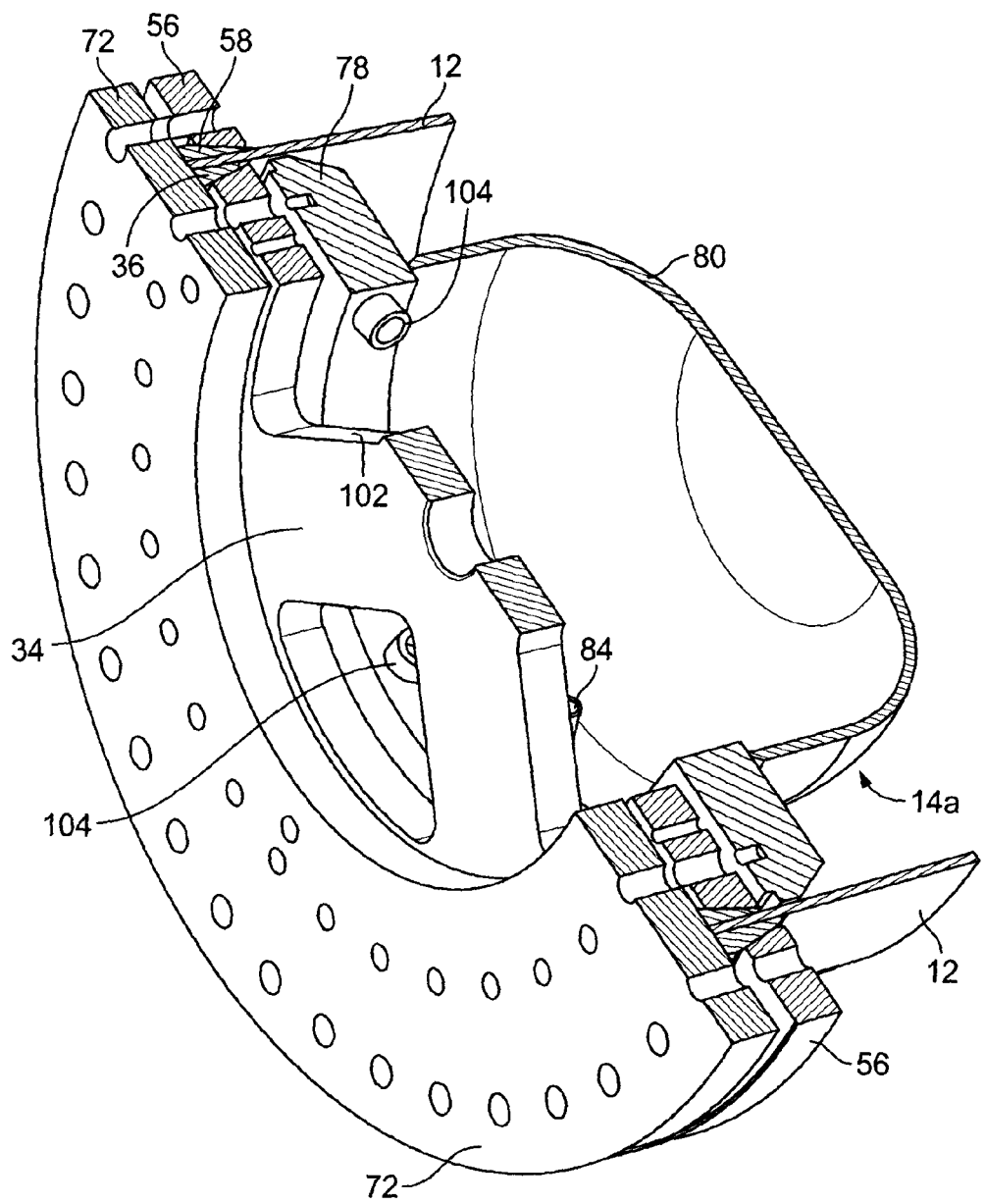
FIG. 34 is a cross sectional perspective view of the apparatus shown in FIG. 25 according to another embodiment.

FIG. 34 illustrates the apparatus of FIG. 32 but without the aforementioned bolts so as to better illustrate the various elements of the apparatus. FIG. 34 also illustrates a further embodiment of the invention wherein a plurality of couplings 104 that are provided on the back plate ring 78 of the back plate 14a. The couplings 104 are used for assisting the placement of the back plate 14a within the pipe 12. The couplings 104 are adapted to receive centering bolts or pins or the like, which serve to bias the back plate 14a against the inner surface of the pipe 12. In one preferred aspect, the couplings 104 are threaded and are adapted to receive correspondingly threaded bolts (not shown). As would be apparent to persons skilled in the art, the bolts, when provided, would be turned so as to be inserted into the end of one of the couplings 104 that is closer to the center of the ring 78. The bolt would then be turned so as to extend radially outwardly from the ring 78 and against the inner surface of the pipe. To balance the ring 78, and therefore the back plate 14a, a number of couplings 104 may be provided around the circumference of the ring 78. In one embodiment, the couplings 104 may be provided in pairs. In another embodiment, six couplings 104 may be provided, with one coupling at each of the top and bottom and two pairs on the sides of the ring 78. It will be understood that the terms "top", "bottom" and "sides" refer to the ring 78 when positioned within a pipe. It will be understood that a variety of numbers and arrangements of the couplings 78 would be possible while providing the same positioning function. In use, the back plate 14a would be positioned within a pipe and the bolts provided in the respective couplings 104 turned so as to allow the back plate 14a to stand freely. The remaining elements of the apparatus may then be positioned and the entire apparatus tightened as described above. During the tightening process, the back plate 14a may be moved towards the front plate 72.

In the above description, reference has been made to the use of bolts and the like for engaging the apparatus of the invention within a pipe. The use of such bolts is illustrated in FIGS. 30 to 32.

Figure 30:
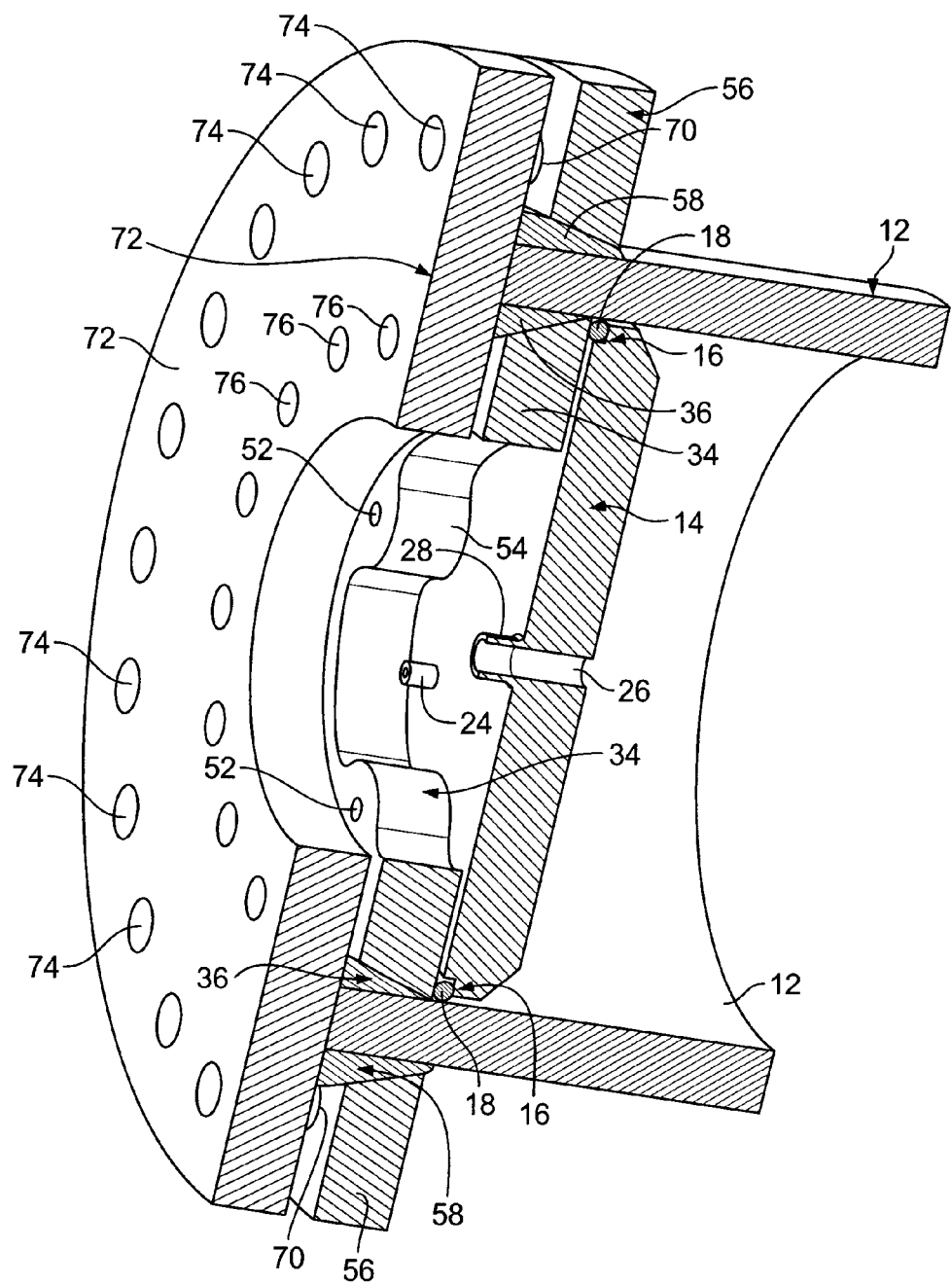
FIG. 30 is a cross sectional perspective view of the apparatus shown in FIG. 1 according to another embodiment.

FIG. 30 illustrates a cross sectional perspective view of an apparatus according to an aspect of the invention. In particular, FIG. 30 provides another view of the apparatus shown in FIG. 1, again without showing the aforementioned first and second bolts, for the purpose of convenience. However, FIG. 31 illustrates the apparatus of FIG. 30 as well as the aforementioned first and second bolts, shown at 90 and 92, respectively. As shown in FIGS. 31 and 30, first bolts 90 extend through bolt holes 76 of the front plate 72, through bolt holes 50 of the inner compression ring 34 (as shown more clearly in FIGS. 7 to 9), and into bolt holes 22 of the back plate 14 (as shown more clearly in FIGS. 2 to 4). As also mentioned above, in one embodiment, the first bolts 90 may be permanently secured to the back plate 14. Once the components of the apparatus 10 as positioned, nuts 94 are then provided on the ends of the first bolts 90 and tightened so as to urge the components together.

FIG. 31 also illustrates the second bolts 92, which extend through the bolt holes 74 of the front plate and through the bolt holes 70 of the second or outer compression ring 56. Nuts 96 and 98 are provided on opposite ends of the second bolts 92. As will be understood, and as described above, tightening of one or both sets of nuts 96, 98 urges the second compression ring 56 and the front plate 72 to together. As described above, and as will be understood, the second bolts 92 may be permanently secured to either of the front plate 72 or the second compression ring 56, thereby avoiding the need for one set of the nuts 96 or 98. It would be possible, in another embodiment, to have alternating second bolts 92 secured to either the front plate 72 or the second compression ring 56, in which case, alternating ones of nuts 96 and 98 may be avoided. Although such an arrangement is possible according to the invention, it will be appreciated that it may not be ideal for ease of use. Nevertheless, various other combinations or embodiments will be possible to achieve the same purpose as described above, namely to urge the front plate 72 and second compression ring 56 together.

As discussed above, the apparatus of the invention is preferably used for sealing an end of a pipe so that the interior of the pipe can be pressurized such as for testing the integrity of the pipe. In one example, the integrity test is used for testing a weld that may be present on the pipe. Such a weld may serve to connect two pipe segments or to connect the pipe to another apparatus. It will also be understood that the apparatus of the invention may be used on both ends of the same pipe. In this way, two apparatuses of the invention may be used on opposite ends of a pipe segment and the above method conducted on such segment.

The above discussion has used geometric terms such as annular, disc, circumference, etc., for ease of reference. However, these terms should not be construed as limiting the invention to any specific shape of nozzle or pipe and various modifications of the apparatus will be apparent to persons skilled in the art to adapt same to any shape or design.

Examples

Specific embodiments of apparatuses according to the present invention will now be described for the purposes of illustration. It will be understood that the following examples are not intended to limit the invention in any way.

Two embodiments of the invention are described below with respect to the use of the apparatus of the invention on a 20" schedule 120 pipe and a 36" schedule 80 pipe. Suggested sizes of the respective components of the apparatus are provided in the Table 1 below.

TABLE 1

| | Size of component (in inches) | |
| --- | --- | --- |
| Component | Apparatus for 20" pipe | Apparatus for 36" pipe |
| Back plate (14) (14a, 78, 80) o.d. | 16.75 | 34.75 |
| Radius of bolt holes (22) on back plate (14) | 14.25 | 30.75 |
| Inner compression ring (34) max. o.d. | 16.67 | 34.75 |
| Radius of outer bolt holes (50) on inner compression ring (34) | 14.25 | 30.75 |
| Radius of inner bolt holes (52) on inner compression ring (34) | 9.25 | 27.5 |
| Inner gripper ring (36) o.d. | 17.0 | 35.0 |
| Inner gripper ring (36) min. i.d. | 15.5 | 33.5 |
| Outer compression ring (56) o.d. | 28.25 | 44.25 |
| Outer compression ring (56) min. i.d. | 20.5 | 36.5 |
| Radius of bolt holes (70) on outer compression ring (56) | 23.75 | 39.5 |
| Outer gripper ring (58) i.d. | 20.0 | 36.0 |
| Outer gripper ring (58) max. o.d. | 21.75 | 37.75 |
| Front plate (72) o.d. | 27.25 | 44.25 |
| Front plate (72) i.d. | 10.417 | |
| Radius of outer bolt holes (74) on front plate (72) | 23.75 | 39.5 |
| Radius of inner bolt holes (76) on front plate (72) | 14.25 | 30.75 |

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference in their entirety.

We claim:

1. An apparatus for sealing an open end of a pipe having a lumen, in connection with fluid pressure testing of the pipe, comprising:
    an annular front plate positioned against the open end face of the pipe, said front plate providing a flange extending outwardly of the pipe;
    a solid back plate positioned transversely within the pipe lumen, said back plate having a front face directed forwardly toward the pipe's open end, a back face directed rearwardly and a perimeter surface defining a clearance with the pipe's inner surface, said back plate being axially movable within the lumen;
    an external gripping means, positioned around the pipe, for compressing inwardly and circumferentially so as to frictionally engage the outer surface of the pipe, said external gripping means comprising an annular external compression ring mounted on a segmental external gripper ring, said rings having oppositely beveled surfaces in contact;

an internal gripping means, positioned within the pipe, for compressing outwardly and circumferentially so as to frictionally engage the inner surface of the pipe, said internal gripping means comprising on annular internal compression ring positioned within a segmental gripper ring, said rings having oppositely beveled surfaces in contact;

said external and internal gripping means being positioned in opposed relationship;

the back plate being positioned directly behind the internal gripping means;

an annular deformable resilient sealing member carried by the back plate along its front edge whereby it may be axially compressed against the internal gripping means;

an outer nut and bolt assembly, connecting the front plate flange with the external compression ring, for pulling the compression ring toward the front plate so as to actuate the external gripping means to frictionally engage the outer surface of the pipe;

an inner nut and bolt assembly, connecting the front plate with the back plate, for pulling the back plate toward the front plate so as to actuate the internal gripping means to frictionally engage the inner surface of the pipe and to deform the sealing member into sealing engagement with the pipe to seal the front end of the clearance;

said back plate forming a pair of ports extending therethrough from its front face to the perimeter surface, one such port terminating at the lower end of the back plate and the other port terminating at its upper end, when in use, whereby the one port may be used to fill the pipe lumen with pressurizing fluid and the other port may be used to vent air from the lumen.

2. A method for sealing and filling the lumen of a pipe having an open end, in preparation for fluid pressure testing of the pipe, comprising:

positioning a circumferentially extending external gripping assembly around the outer surface of the pipe;

transversely positioning an axially movable, solid, back plate, having front, back and perimeter surfaces, and a circumferentially extending internal gripping assembly within the pipe lumen, said back plate carrying a deformable, resilient, annular sealing member along its front edge and being positioned directly behind the internal gripping assembly;

positioning an annular front plate against the end face of the pipe's open end;

separately connecting the front plate with each of the outer gripping assembly and the back plate using outer and inner threaded nut and bolt means respectively;

actuating the external gripping assembly by tightening the outer nut and bolt means so that said gripping assembly compresses inwardly against the outer surface of the pipe and frictionally engages said outer surface;

tightening the inner nut and bolt means to pull the back plate toward the front plate and thereby compress the sealing member against the internal gripping assembly, so that said sealing member deforms into sealing engagement with the inner surface of the pipe, and to cause the internal gripping assembly to expand outwardly to compress against the inner surface of the pipe and frictionally engage said surface; and filling the pipe lumen with pressure-testing fluid by conveying it through a first port extending through the back plate from its front surface to the lower end of its perimeter surface and simultaneously venting displaced air from the pipe lumen through a second port extending through the back plate from the upper end of its perimeter surface to its front surface.

* * * * *